US009632065B2

(12) United States Patent
Gamache

(10) Patent No.: US 9,632,065 B2
(45) Date of Patent: Apr. 25, 2017

(54) DIAPHRAGM VALVE WITH SEALING ASSEMBLY, CHROMATOGRAPHIC SYSTEM INCLUDING SAME AND METHOD OF OPERATION THEREOF

(71) Applicant: MÉCANIQUE ANALYTIQUE INC., Thetford-Mines (CA)

(72) Inventor: Yves Gamache, Thetford-Mines (CA)

(73) Assignee: MÉCANIQUE ANALYTIQUE INC., Thetford-Mines (Québec) (CA)

( * ) Notice: Subject to any disclaimer, the term of this patent is extended or adjusted under 35 U.S.C. 154(b) by 44 days.

(21) Appl. No.: 14/775,195

(22) PCT Filed: Mar. 11, 2014

(86) PCT No.: PCT/CA2014/050208
§ 371 (c)(1),
(2) Date: Sep. 11, 2015

(87) PCT Pub. No.: WO2014/138966
PCT Pub. Date: Sep. 18, 2014

(65) Prior Publication Data
US 2016/0025688 A1    Jan. 28, 2016

Related U.S. Application Data

(60) Provisional application No. 61/776,300, filed on Mar. 11, 2013, provisional application No. 61/787,050, (Continued)

(51) Int. Cl.
*F16K 11/00*    (2006.01)
*G01N 30/20*    (2006.01)
(Continued)

(52) U.S. Cl.
CPC .............. *G01N 30/20* (2013.01); *F16K 11/00* (2013.01); *F16K 11/022* (2013.01);
(Continued)

(58) Field of Classification Search
USPC ......................................................... 137/597
See application file for complete search history.

(56) References Cited

U.S. PATENT DOCUMENTS 4,333,500 A    6/1982  Broerman
5,950,674 A *  9/1999  Wylie ....................... F16K 7/17
                                                    137/597

(Continued)

FOREIGN PATENT DOCUMENTS

CA    2221528        5/1998
CA    2718301 A1    8/2006
(Continued)

OTHER PUBLICATIONS

Thomas Muller, Supplementary European Search Report, Nov. 2, 2016.

*Primary Examiner* — John Fox
(74) *Attorney, Agent, or Firm* — Price Heneveld LLP

(57) ABSTRACT

A valve having a valve cap with a plurality of process conduits extending therethrough, each one of the plurality of process conduits ending in a process port at a valve cap interface. The valve also has a valve body defining a valve body interface facing the valve cap interface, a diaphragm positioned between the valve cap interface and the valve body interface, across the process ports, and a purge line provided through one of the valve cap and the valve body. The valve further comprises a sealing assembly located in the valve body. The sealing assembly is configured and positioned to block fluid leaked through the diaphragm such that the fluid leaked through the diaphragm is discharged via and exit of the purge line of the valve. A chromatographic system including the valve and a method of operation thereof are also provided.

23 Claims, 24 Drawing Sheets

Related U.S. Application Data filed on Mar. 15, 2013, provisional application No. 61/839,581, filed on Jun. 26, 2013.

(51) Int. Cl.
*F16K 11/02* (2006.01)
*F16K 27/02* (2006.01)
*G05D 7/06* (2006.01)

(52) U.S. Cl.
CPC ....... *F16K 27/0236* (2013.01); *G05D 7/0635* (2013.01); *G01N 2030/202* (2013.01); *G01N 2030/205* (2013.01)

(56) References Cited

U.S. PATENT DOCUMENTS

| | | | |
|---|---|---|---|
| 6,742,544 B2 | 6/2004 | Bergh et al. | |
| 7,216,528 B2 * | 5/2007 | Gamache | F16K 7/14 137/240 |
| 7,931,043 B2 * | 4/2011 | Gamache | F16K 11/20 137/15.04 |
| 8,469,057 B2 * | 6/2013 | Gamache | F16K 11/20 137/316 |
| 8,794,594 B2 * | 8/2014 | Gamache | F16K 7/16 137/597 |
| 8,851,452 B2 * | 10/2014 | Gamache | F16K 7/16 137/597 |
| 9,377,444 B2 * | 6/2016 | Gamache | F16K 11/20 |
| 2009/0179169 A1 | 7/2009 | Fleming | |

FOREIGN PATENT DOCUMENTS

| | | |
|---|---|---|
| EP | 2244091 | 10/2010 |
| WO | 2006021071 A1 | 3/2006 |
| WO | 2006089389 A1 | 8/2006 |
| WO | 2008089583 A1 | 7/2008 |
| WO | 2009006742 A1 | 1/2009 |
| WO | 2009073966 A1 | 6/2009 |
| WO | 2010025570 A1 | 3/2010 |
| WO | 2010063125 A1 | 6/2010 |
| WO | 2010111791 A1 | 10/2010 |
| WO | 2013010269 A1 | 1/2013 |

\* cited by examiner

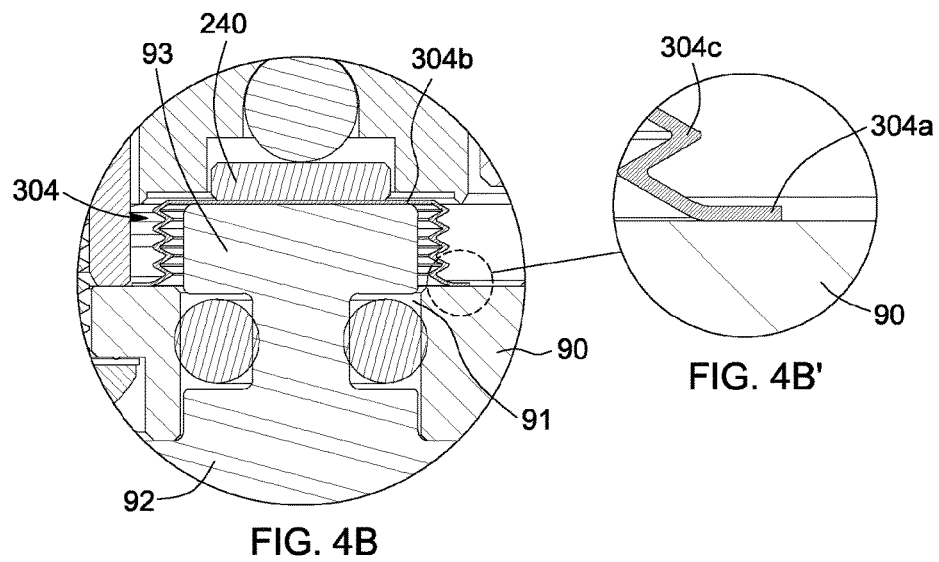
FIG. 4B
FIG. 4B'
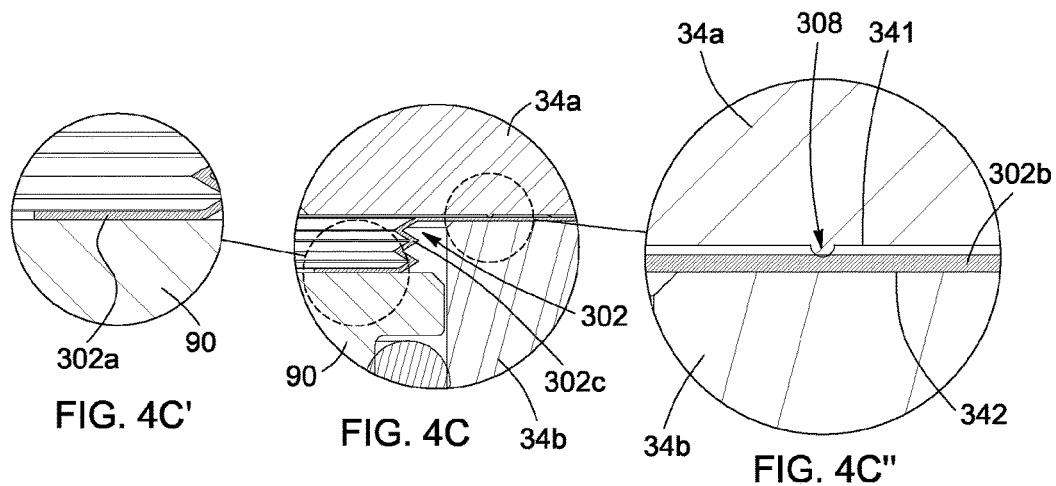
FIG. 4C'
FIG. 4C
FIG. 4C"
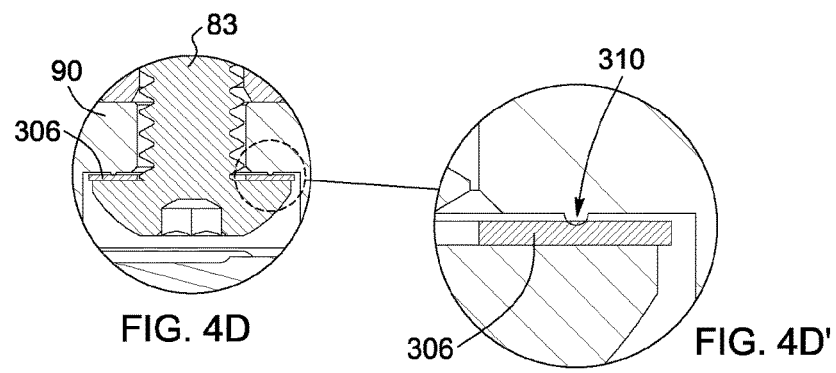
FIG. 4D
FIG. 4D'

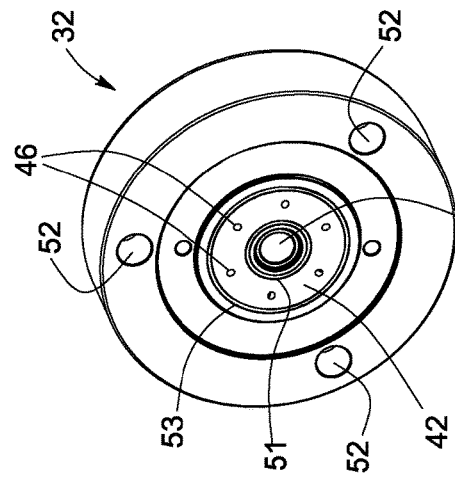
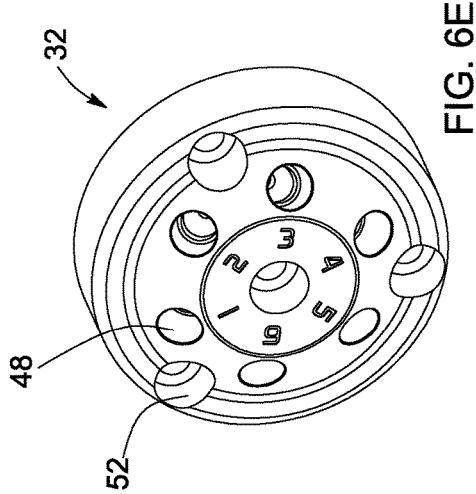
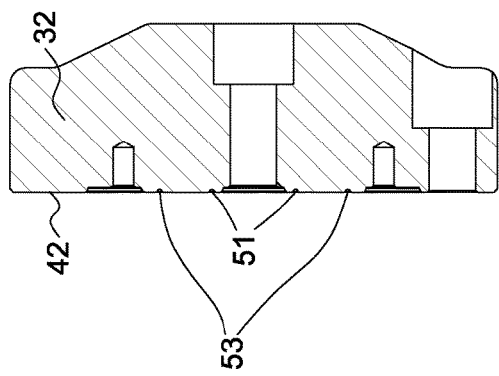
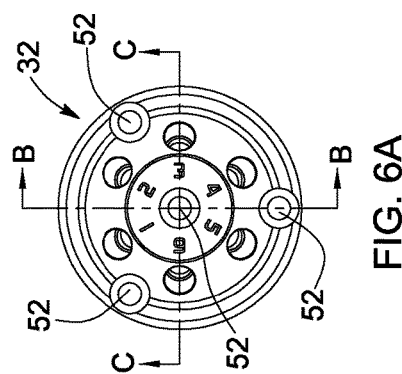
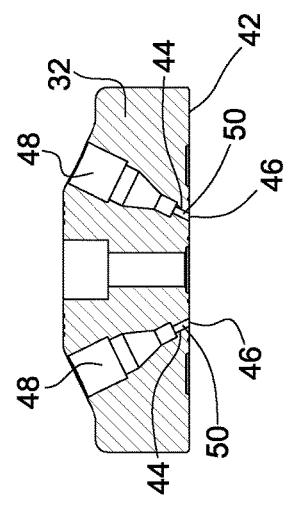

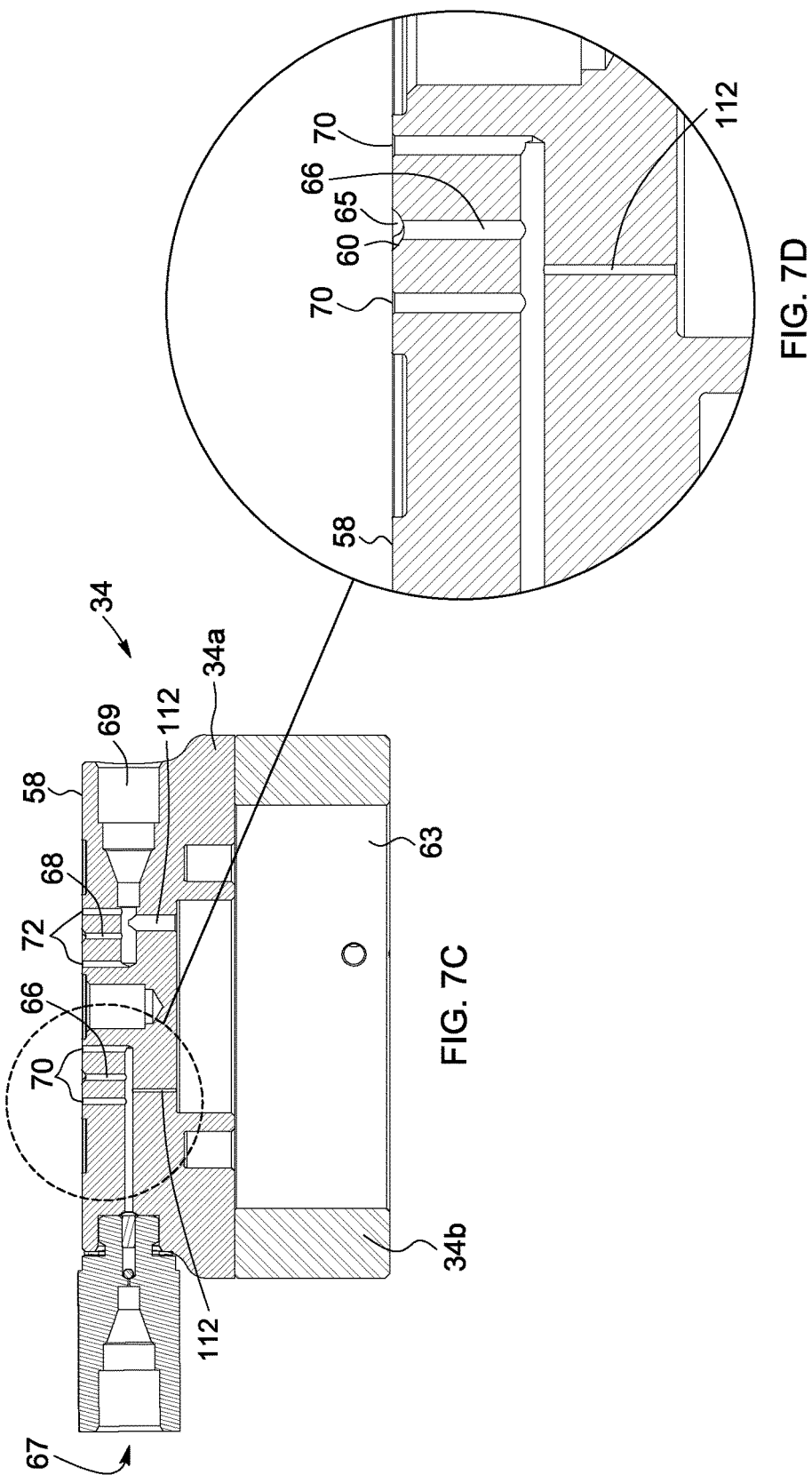

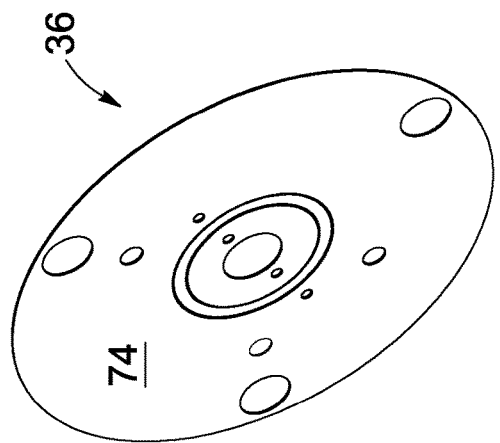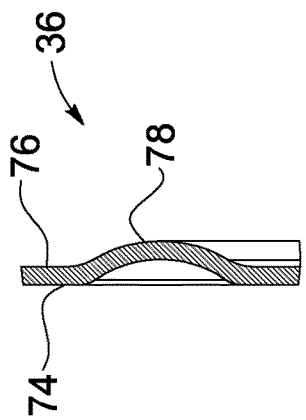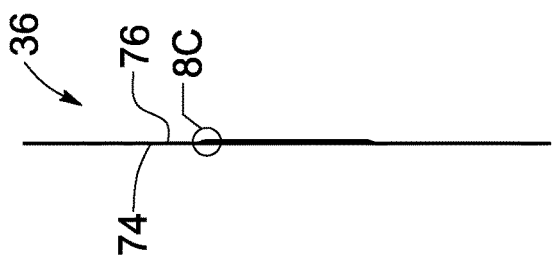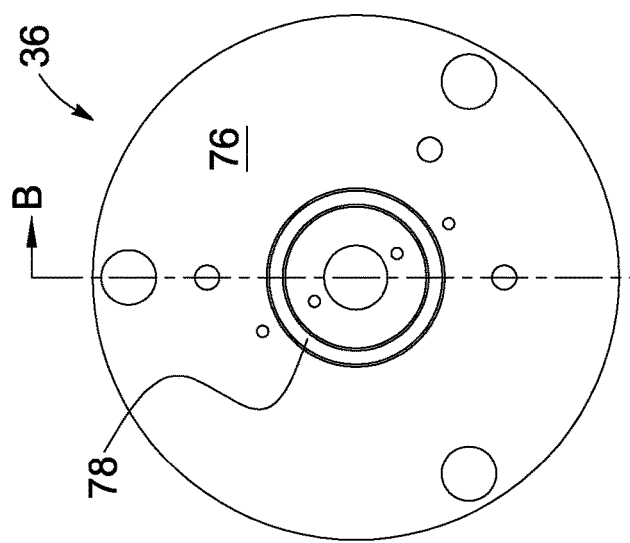

DIAPHRAGM VALVE WITH SEALING ASSEMBLY, CHROMATOGRAPHIC SYSTEM INCLUDING SAME AND METHOD OF OPERATION THEREOF

FIELD OF THE INVENTION

The present invention generally relates to fluid analytical systems and more particularly concerns a diaphragm-sealed valve having a sealing assembly for sealing the actuating mechanism of the actuation system from potential gas leaks through the diaphragm and being operative to discharge the fluid leaked through the diaphragm via the exit of a purge line of the valve, as well as a chromatographic system including same and method of operation thereof.

BACKGROUND

As well known by those skilled in the art, chromatographic systems rely on the use of valves to allow reproducible sample introduction and various column switching schemes.

Diaphragm valves of various designs are known in the art for chromatography applications. Such diaphragm valves have been used in many commercially available gas chromatographs. They are apt to be integrated more easily in a gas chromatograph due to their physical size and since the actuator is embedded in the valve itself. These characteristics make them attractive for gas chromatograph manufacturers.

Referring to FIG. 1 (PRIOR ART), there is shown an example of a typical diaphragm-sealed valve as known in the art. The valve 1 is provided with a top block 2 having an interface 4 and a plurality of ports 6. Each one of the ports 6 opens at the interface 4 and has a thread passage 8 to connect various analytical fitting and tubing (not shown). At the bottom of the thread passage 8, there is a conduit 10 extending in the top block 2 and opening into the ports 6 at the interface 4. The ports 6 are arranged along a line, such as, for example, a circular line, on the interface 4 of the top block 2. The interface 4 is advantageously flat and polished to minimize leaks between ports 6 and from the ambient atmosphere. The valve 1 is also provided with a bottom block 12 and a diaphragm 14, which is generally made of material such as polyimide, Teflon™ (polytetrafluoroethylene) or other polymers. The diaphragm 14 is positioned between the top block interface 4 and the bottom block 12, and has a recess 18 therein extending along a line formed by the ports 6 and biased away from the interface 4 of the top block 2. The recess 18 in the diaphragm 14 sits in a matching recess 20 made in the bottom block 12, thereby allowing some clearance for fluid circulation between adjacent ports 6.

The valve 1 is also provided with a plurality of plungers 16 mounted in the bottom block 12, each one of the plungers 16 being respectively arranged to compress the diaphragm 14 against the top block 2 at a position located between two of the ports 6. Preferably and as illustrated, in the case of a six port valve, when the valve is at rest, three plungers 16 are up while the other three are down. When the plungers 16 are up, they compress the diaphragm 14 against the top block 2 and close the conduits made by the diaphragm recess 18, so that fluid circulation is blocked. The bottom block 12 keeps the plungers 16 and the actuation system moving the plungers 16 between the up and down configurations, in position.

It is common to designate a portion of the plungers 16 as "normally open" and another portion of the plungers 16 as "normally closed". A normally open plunger 16 is biased downwards, i.e. away from the diaphragm 14, and therefore normally allows fluid circulation between the two adjacent ports 6. A normally closed plunger 16 is biased upwards, i.e. towards the diaphragm 14, and therefore blocks fluid circulation between the two adjacent ports 6. The valve 1 may be actuated in order to alter the positions of the plungers 16, for example by sliding upwards and downwards the normally open and normally closed plungers 16, respectively.

In many cases a gas sampled by the diaphragm-sealed valve or a carrier gas used to carry the sample gas can be a corrosive, a toxic, an unstable and/or a reactive gas. For example and without being limitative, the gas may comprise hydrogen fluoride, silane, phosphine, ammonia, chlorine, boron trichloride, nitrogen trifluoride, fluorine, bromine, hydrogen, arsine, phosphine or the like. When such gases are used with known gas chromatograph diaphragm valve, the gases are isolated from the actuation system of the valve, and the ambient air by the diaphragm.

However, over time, the diaphragm could be punctured, for example due to material aging, over-pressure operation, high velocity abrasion, sample contamination and/or by-products generation. When the diaphragm is punctured, undesirable leak of the sample and/or the carrier gas into the actuating mechanism of the actuation system of the valve, or release of the gas into the ambient air may occur. Moreover, using known valve, such leaks are difficult to detect promptly in order to initiate desirable actions.

Depending of the nature of the sample and/or the carrier gas, this could result in undesirable damage to the valve, the instrument where the valve is installed or to auxiliary equipment used to control the valve. Those skilled in the art know to take great care when dealing with such gases, and a careful control of the environment in which they are used is performed.

It is known to use o-rings between the components in order to reduce the potential flow of gas between components of the valve, subsequently to a leak through the diaphragm. However, the use of o-rings often proves to be unsatisfying when the leaked sampling and/or carrier gas is a corrosive, a toxic, an unstable and/or a reactive gas.

In view of the above, there is a need for an improved valve, chromatographic system using the same and a method of operation thereof which, would be able to overcome or at least minimize some of the above-discussed prior art concerns.

SUMMARY OF THE INVENTION

According to a first general aspect, there is provided a valve which comprises a valve cap having a plurality of process conduits extending therethrough, each one of the plurality of process conduits ending in a process port at a valve cap interface. The valve also comprises a valve body defining a valve body interface facing the valve cap interface, a diaphragm positioned between the valve cap interface and the valve body interface, across the process ports, and a purge line provided through one of the valve cap and the valve body. The purge line has an entry and an exit. The valve further comprises a sealing assembly located in the valve body. The sealing assembly is configured and positioned to block fluid leaked through the diaphragm such that the fluid leaked through the diaphragm is discharged via the exit of the purge line of the valve.

In an embodiment, the valve further comprises a check valve preventing an upstream flow of fluid leaked through the diaphragm into the entry of the purge line.

In an embodiment, the valve body has a plurality of plunger passages extending therein and the sealing assembly comprises a plurality of passage seals, each one of the plurality of passage seals sealing a corresponding one of the plurality of plunger passages.

In an embodiment, valve body comprises an upper section and a lower section, each one of the plurality of passage seals sealing the corresponding one of the plurality of plunger passages at an interface between the upper section and the lower section of the valve body.

In an embodiment, the valve further comprises a plurality of plungers having a base section and a top section, each one of the plurality of plungers being positioned in a corresponding plunger passage of the plurality of plunger passages and each one of the passage seals covering the base section of a corresponding one of the plurality of plungers by extending between the base section and the top section of the plunger, in the corresponding plunger passage.

In an embodiment, the sealing assembly comprises a sealing diaphragm including the plurality of passage seals, the sealing diaphragm being positioned between the upper section and the lower section of the valve body.

In an embodiment, each one of the plurality of passage seals is configured to expand and retract according to the movement of the base section of the corresponding one of the plurality of plungers.

In an embodiment, each one of the plurality of passage seals comprises a bellows section.

In an embodiment, each one of the plurality of passage seals biases the base section of the corresponding one of the plurality of plungers downwards, thereby cooperating with the biasing mechanism to bias the plunger towards an open configuration.

In an embodiment, the sealing diaphragm is a metallic diaphragm.

In an embodiment, the sealing diaphragm is coated with a protective coating.

In an embodiment, the valve further comprises a plurality of plungers. Each one of the plurality of plungers is positioned in a corresponding plunger passage of a plurality of plunger passages formed in the valve body and is movable between a closed position where the plunger engages the diaphragm, and an open position where the plunger is disengaged from the diaphragm. The valve also comprises an actuation system for moving each one of the plurality of plungers between the closed position and the open position, the actuation system comprising an upper piston and a lower piston. The sealing assembly comprises a first seal for sealing an interface between the upper piston and the valve body, a second seal for sealing an interface between the upper piston and the lower piston; and a plurality of third seals for sealing a connection between the upper piston and each one of the plurality of plungers mounted thereto.

In an embodiment, the first seal is connected at a first end to the upper piston and at a second end to the valve body, the second seal is connected to the upper piston and covers a section of the lower piston extending through the upper piston and each one of the plurality of third seals is located between the upper piston and a head of a mounting mean for mounting one of the plurality of plungers thereto.

In an embodiment, each one of the first seal, the second seal and the plurality of third seals are metallic seals.

In an embodiment, at least one of the first seal, the second seal and one of the plurality of third seals is coated with a protective coating.

In an embodiment, at least one of the first seal and the second seal further comprise a bellows section.

According to another general aspect, there is also provided a chromatographic system which comprises a valve and a monitoring system. The valve comprises a valve cap having a plurality of process conduits extending therethrough, each one of the plurality of process conduits ending in a process port at a valve cap interface. The valve also comprises a valve body defining a valve body interface facing the valve cap interface, a diaphragm positioned between the valve cap interface and the valve body interface, across the process ports and a purge line provided through one of the valve cap and the valve body. The purge line has an entry and an exit. The valve further comprises a sealing assembly located in the valve body. The sealing assembly is configured and positioned to block fluid leaked through the diaphragm such that the fluid leaked through the diaphragm is discharged via the exit of the purge line of the valve. The monitoring system is connected to the exit of the purge line of the valve and is configured to monitor a purge gas flowing through the exit of the purge line, detect variations of the purge gas indicative of a fluid leaked through the diaphragm of the valve and trigger a leak control procedure upon detection of the variations of the purge gas indicative of a fluid leaked through the diaphragm of the valve.

In an embodiment, the valve further comprises a check valve preventing an upstream flow of fluid leaked through the diaphragm into an entry of the purge line.

According to another general aspect, there is also provided a method of operation of a chromatographic system including a valve such as defined above. The method comprises the steps of: monitoring a purge fluid flowing through an exit of a purge line of the valve; detecting variations of the purge fluid indicative of a fluid leaked through the diaphragm of the valve; and triggering a leak control procedure upon detection of the variations of the purge fluid indicative of a fluid leaked through the diaphragm of the valve.

In an embodiment, the step of monitoring a purge fluid flowing through an exit of a purge line of the valve includes at least one of monitoring a pressure of the purge fluid and monitoring a purity of the purge fluid.

In an embodiment, the step of triggering a leak control procedure upon detection of the variations of the purge fluid indicative of a fluid leaked through the diaphragm of the valve includes at least one of initiating the shutting of a fluid supply of the valve, releasing an inert fluid into the valve and activating a signal indicative of a leak.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIG. 4B is an enlarged view of section 4B of FIG. 4.

FIG. 4B' is an enlarged view of a section of FIG. 4B.
FIG. 4C is an enlarged view of section 4C of FIG. 4.
FIG. 4C' is an enlarged view of a section of FIG. 4C.
FIG. 4D'' is an enlarged view of a section of FIG. 4C.
FIG. 4D is an enlarged view of section 4D of FIG. 4.
FIG. 4D' is an enlarged view of a section of FIG. 4D.
FIG. 6A is a top view of a valve cap according to an embodiment.
FIG. 6B is a cross-sectional side view of the valve cap of FIG. 6A taken along line B-B.
FIG. 6C is a cross-sectional view of the valve cap of FIG. 6A taken along the line C C.
FIGS. 6D and 6E are a bottom perspective view and a top perspective view of the valve cap of FIG. 6A, respectively.
FIG. 7C is a cross-sectional side view of the cylinder of FIG. 7A taken along line 7C 7C.
FIG. 7D is an enlarged view of a section of FIG. 7C.
FIG. 8A is a bottom view of a diaphragm according to an embodiment.
FIG. 8B is a cross-sectional side view of the diaphragm of FIG. 8A taken along line B-B.
FIG. 8C is an enlarged view of section 8C of FIG. 8B.
FIG. 8D is a top perspective view of the diaphragm of FIG. 8A.

DETAILED DESCRIPTION

Figure 1:
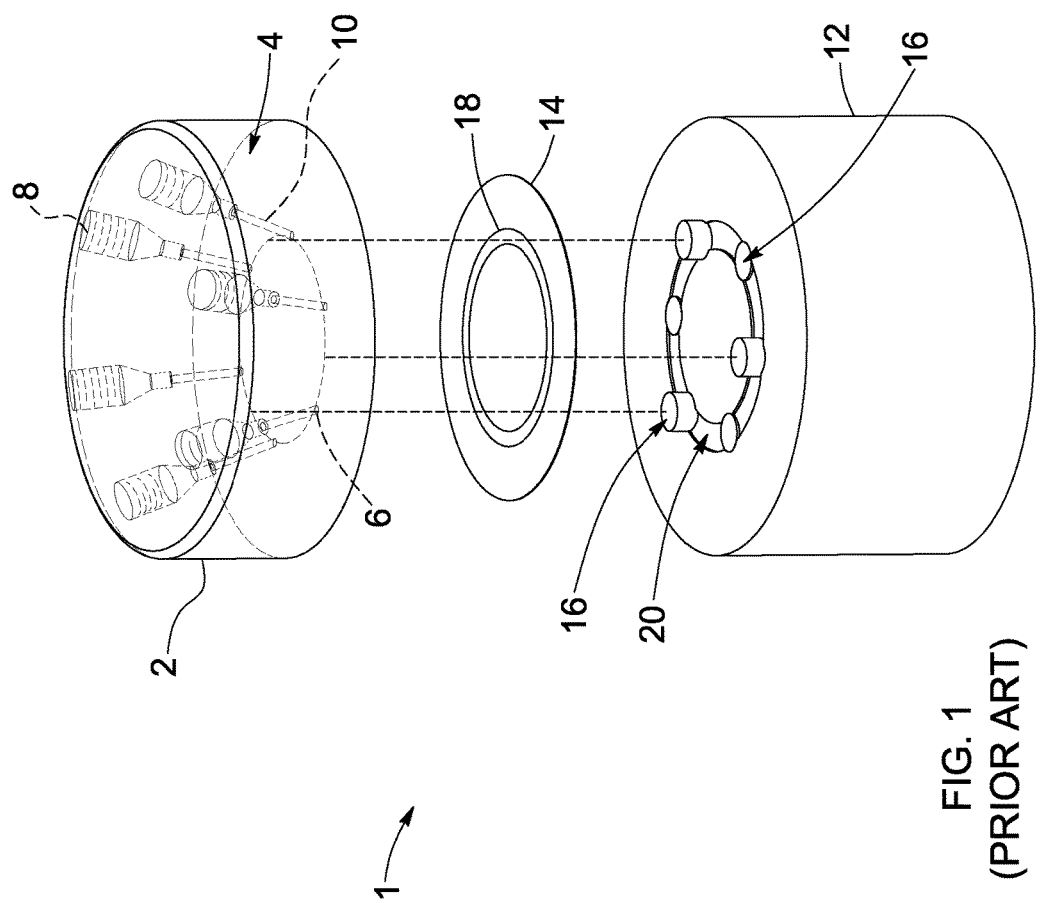
FIG. 1 (PRIOR ART) is an exploded perspective view of a diaphragm-sealed valve known in the art, in partial transparency.
Figure 2:
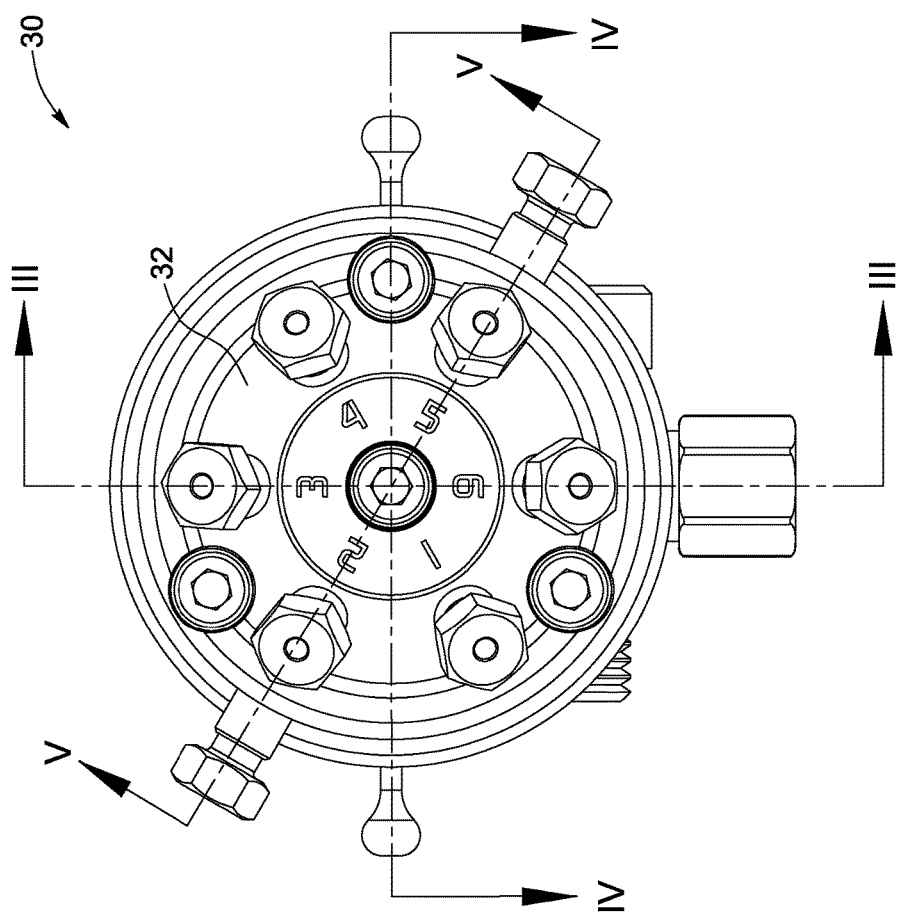
FIG. 2 is a top view of a diaphragm-sealed valve according to an embodiment.

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of the valve and the chromatographic system and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the valve and the chromatographic system, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

In addition, even though in the course of the present application the valve is described in relation with gases, such as a sampling gas, a carrier gas, a purge gas and an actuation gas, one skilled in the art will understand that, in alternative embodiments, the valve may be used in relation with other fluids different than a gas. Indeed, one skilled in the art will understand that, for example and without being limitative, the valve may be used in relation with liquids rather than gases.

Referring generally to FIGS. 2 to 5 there is shown a valve 30 of the diaphragm-sealed type, according to an embodiment. Such a valve 30 may be used in analytical equipments of various types, and more particularly in chromatographic equipment or online analyzers.

As illustrated in FIGS. 2 to 5, the valve 30 includes five main elements: a valve cap 32, a valve body 33, a diaphragm 36 compressibly positioned between the valve cap 32 and the valve body 33, a plurality of plungers 82 and an actuation system 220.

In an embodiment, the valve body 33 is formed of a cylinder 34 and a bottom cap 40 or other equivalent structures allowing the plurality of plungers 82 and the actuating mechanism 96 of the actuation system 220 to be mounted to the valve body 33. The combination of the valve cap 32, the cylinder 34, the diaphragm 36 and the plurality of plungers 82 may be referred to as the process assembly 301.

Valve Cap

Figure 3:
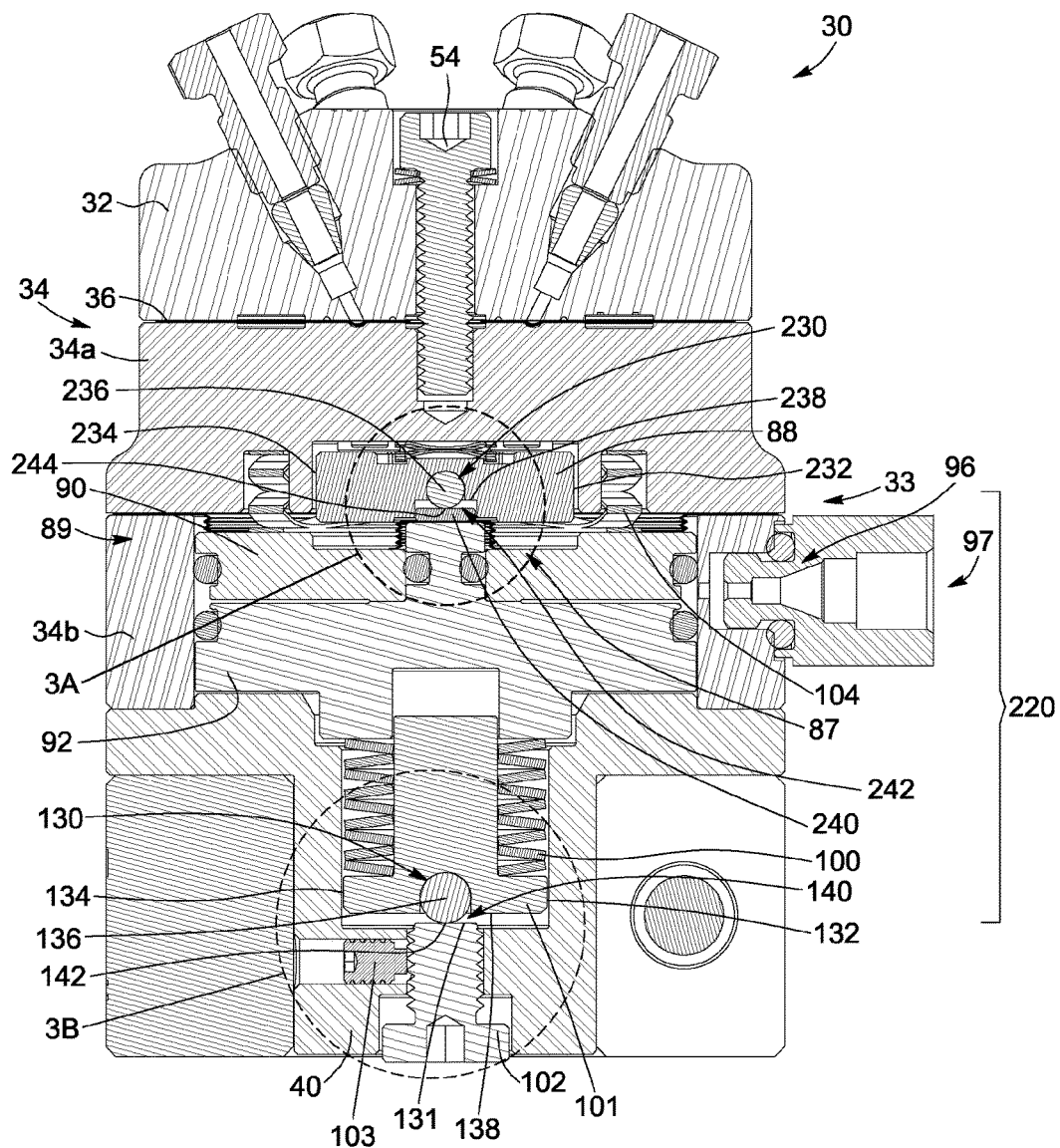
FIG. 3 is a cross-sectional side view of an embodiment of the diaphragm-sealed valve of FIG. 2 taken along line III-III.
Figure 4:
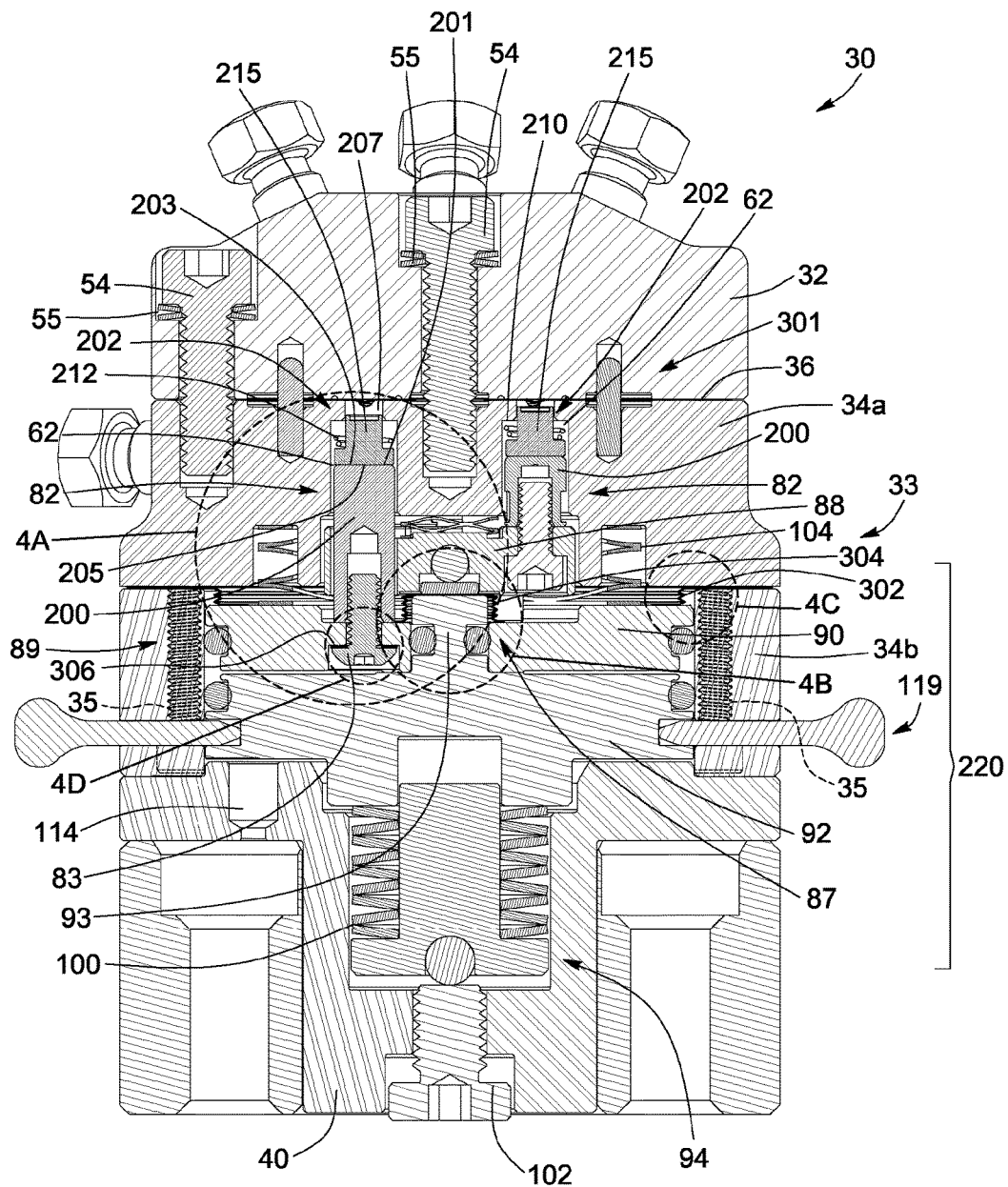
FIG. 4 is a cross-sectional side view of an embodiment of the diaphragm-sealed valve of FIG. 2 taken along line IV-IV.
Figure 4A:
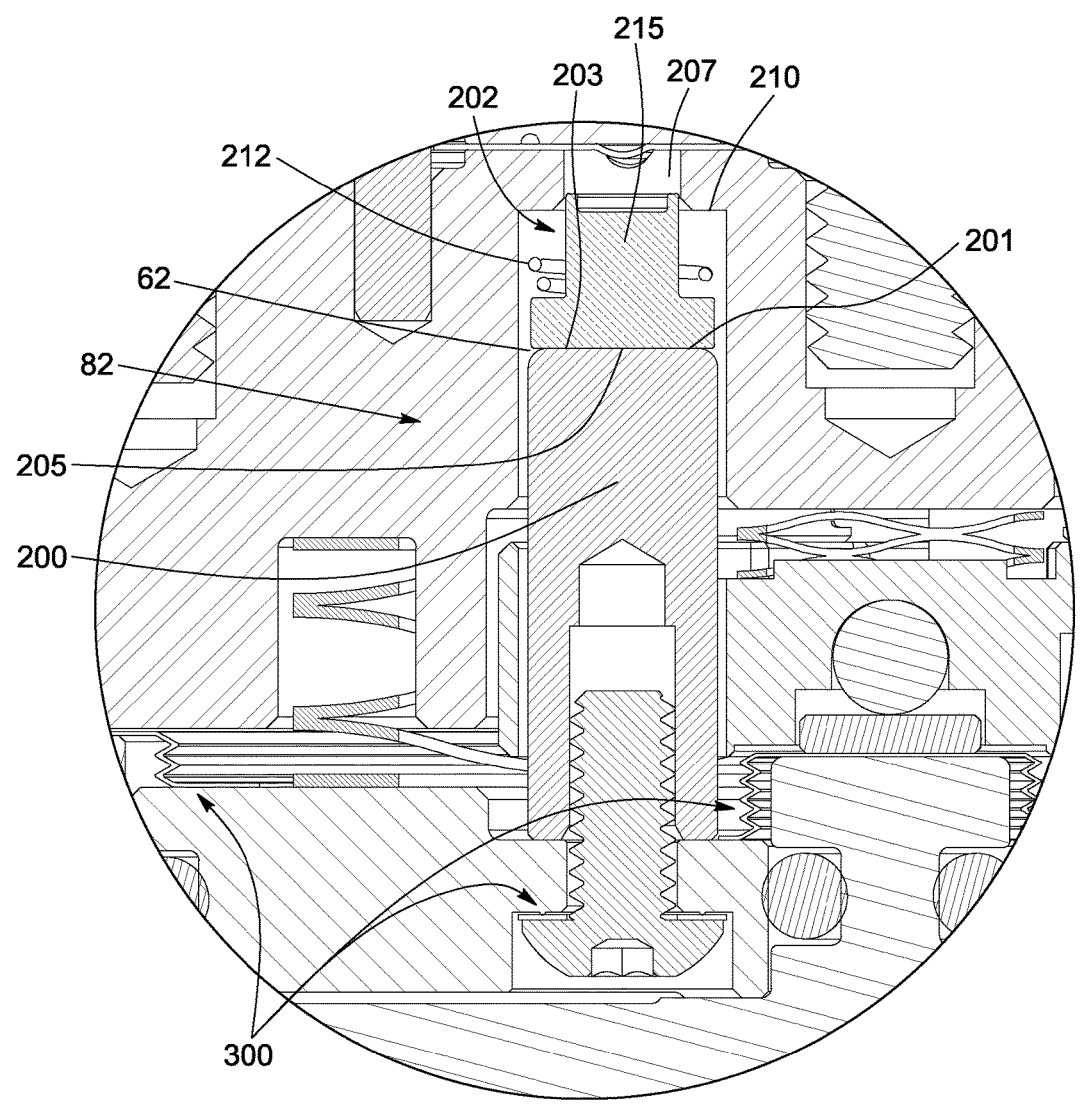
FIG. 4A is an enlarged view of section 4A of FIG. 4.
Figure 5:
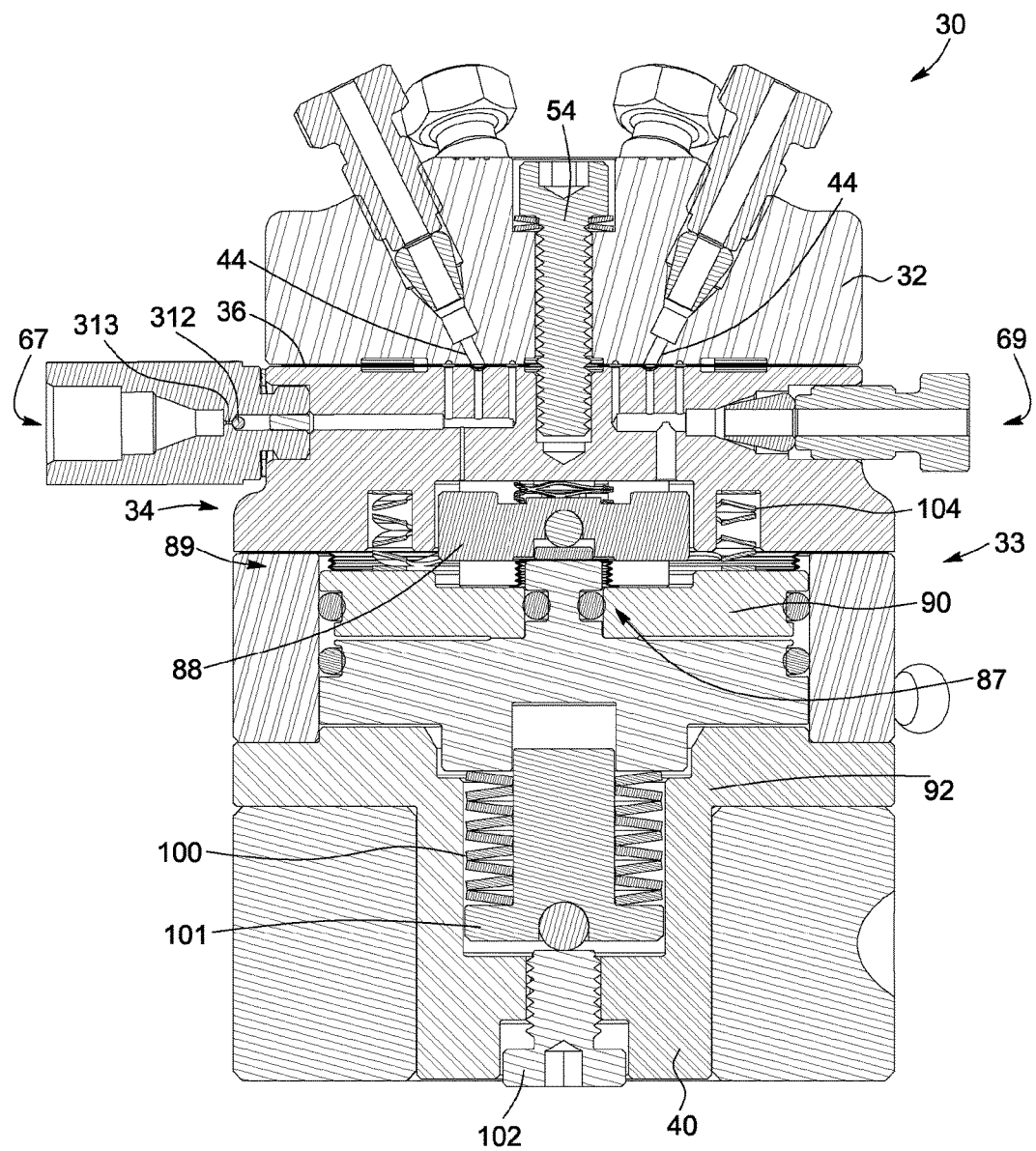
FIG. 5 is a cross-sectional side view of an embodiment of the diaphragm-sealed valve of FIG. 2 taken along line V-V.

Still referring to FIGS. 2 to 5 and additionally to FIGS. 6A to 6E, there is shown a valve cap 32 according to an embodiment. In the illustrated embodiment, the valve cap 32 has a plurality of process conduits 44 extending through it and an interface, hereinafter referred to as the valve cap interface 42. In an embodiment, the valve cap interface 42 is flat and smooth, and is in contact with the diaphragm 36 when the valve 30 is assembled (as shown in FIGS. 3 to 5).

Each process conduit 44 ends in a process port 46 opening at the valve cap interface 42. In an embodiment, the process ports 46 are circularly arranged on the valve cap interface 42.

Best shown in FIG. 6C, in an embodiment, each one of the process conduits 44 is formed by a larger threaded hole 48 for receiving tubing connections and a smaller fluid passage 50 ending in the process port 46.

In the illustrated embodiment, the valve cap 32 has a cylindrical shape and is, for example and without being limitative, made of electro-polished stainless steel. The valve cap 32 is also provided with screw holes 52 for receiving socket head cap screws 54, for mounting the valve cap 32 to the cylinder 34. As can be seen on FIG. 4, in an embodiment, a biasing mechanism 55 such as, without being limitative, a Belleville washer stack, is provided between the head of the socket head cap screws 54 and the screw holes 52, in order to maintain a constant pressure on the diaphragm 36, between the valve cap 32 and the cylinder 34, independently of the temperature variation to which the valve 30 may be subject to.

Of course, in alternative embodiments, other arrangements for holding the valve cap 32 to the cylinder 34 can be considered. Optionally, in an alternative embodiment, a layer of polymer may cover the valve cap interface 42 of the valve cap 32. Moreover, in alternative embodiments, other materials, for example and without being limitative, ceramic or various types of polymers, may be used as material for the valve cap 32 or a portion thereof. One skilled in the art will readily understand that the valve cap 32 may present a different shape, form or configuration than the cylindrical one shown in the embodiment illustrated in the Figures. Of course, other embodiments of the valve cap may include four, eight, ten, twelve or any other convenient number of process ports 46.

Cylinder

Now referring to FIGS. 3 to 5 and 7A to 7D, there is shown, for illustrative purposes, one embodiment of the cylinder 34 of the body 33 of the valve 30. Similarly to the valve cap 32 described above, the cylinder 34 also has an interface, hereinafter referred to as the valve body interface 58, which faces the valve cap interface 42 of the valve cap 32 when the valve is assembled (as shown in FIGS. 3 to 5). Once again, in an embodiment, the valve body interface 58 is smooth and flat. The valve body interface 58 is provided with a main recess 60 having an outline matching the arrangement of the process ports 46 on the valve cap interface 42. Therefore, in the illustrated embodiment where the process ports 46 are circularly arranged on the valve cap interface 42, the main recess 60 presents a circular outline. The main recess 60 is aligned with the process ports 46 of the valve cap 32 when the valve elements are assembled and the valve 30 is ready for use (as shown in FIGS. 3 to 5).

The cylinder 34 also includes a plurality of plunger passages 62 each extending in the cylinder 34 and opening at one end in the main recess 60, between two of the process ports 46. The other ends of the plunger passages 62 open in a valve body cavity 63.

Figure 7B:
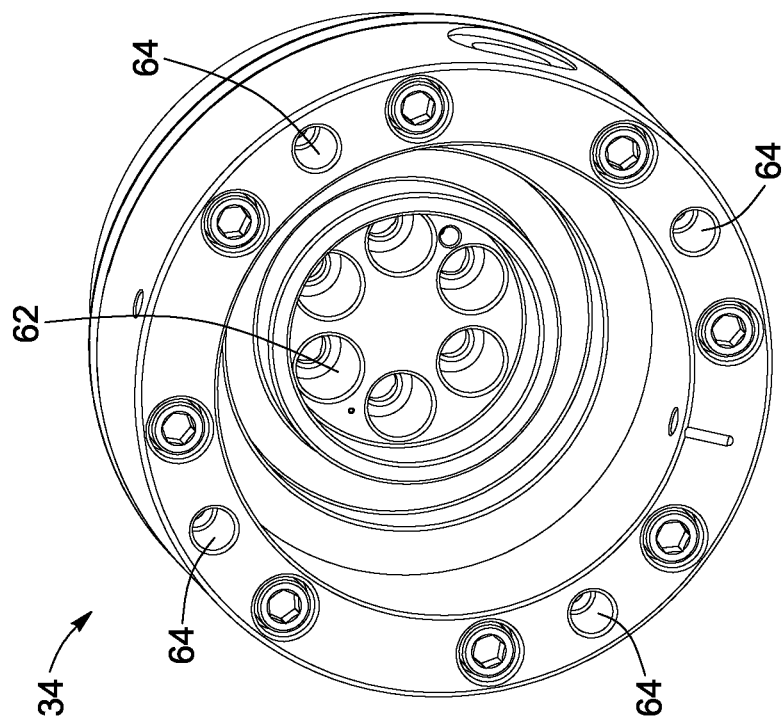
FIG. 7B is a bottom perspective view of the cylinder of FIG. 7A.
Figure 7A:
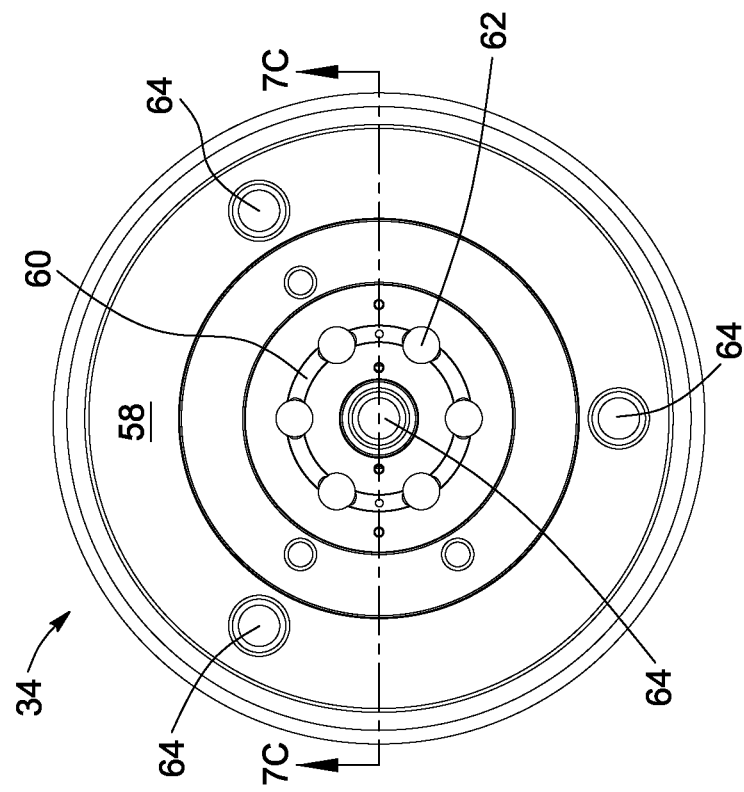
FIG. 7A is a top view of a cylinder of the valve body according to an embodiment.

The cylinder 34 is also provided with a first set of screw holes 64 for receiving the socket head cap screws 54 that hold the cylinder 34 to the valve cap 32 (best shown in FIG. 7A) and a second set of screw holes 64 for receiving the socket head cap screws that hold the cylinder 34 to the bottom cap 40 (best shown in FIG. 7B). Of course, in alternative embodiments, other arrangements could be considered for affixing the cylinder 34 to the valve cap 32 or the bottom cap 40.

As can be seen in FIGS. 3, to 5, in an embodiment the cylinder 34 is formed of an upper section 34a and a lower section 34b. In an embodiment, the upper section 34a of the cylinder 34 and the lower section 34b of the cylinder 34 are connected to one another by a plurality of cylinder body screws 35 which can be used to adjust the pressure between the upper section 34a and the lower section 34b of the cylinder 34.

Figure 10:
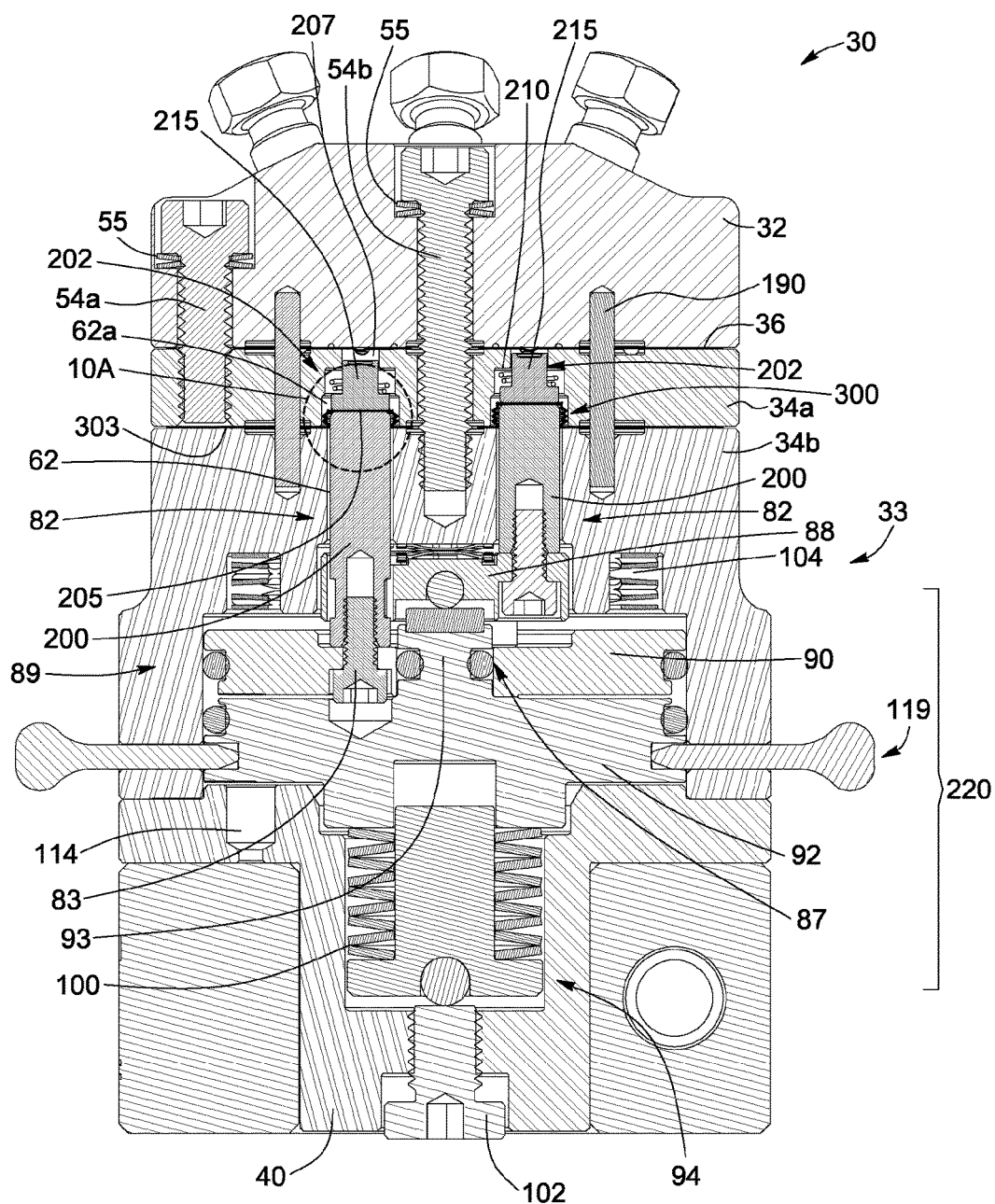
FIG. 10 is a cross-sectional side view of another embodiment of a diaphragm-sealed valve according to an embodiment.

Now referring to FIG. 10, in an alternative embodiment the cylinder 34 is also formed of an upper section 34a and a lower section 34b, but in the illustrated embodiment the upper section 34a is thinner than the upper section 34a of the embodiment shown in FIGS. 3 to 5. In the embodiment shown in FIG. 10, the upper section 34a of the cylinder 34 and the lower section 34b of the cylinder 34 are connected to one another by a combination of peripheral socket head cap screws 54a holding the upper section 34a of the cylinder 34 to the valve cap 32 and a central socket head cap screw 54b extending through the upper section 34a of the cylinder 34 and holding the lower section 34b of the cylinder 34 to the valve cap 32. In an embodiment, alignment pins 190 extending through the upper section 34a of the cylinder 34 and into the lower section 34b of the cylinder 34 and the valve cap 32 may further be provided.

Diaphragm

Now referring to FIGS. 8A to 8D, there is shown an embodiment of the diaphragm 36 of the valve 30. The diaphragm 36 has a first surface 74 facing the valve cap 32 and a second surface 76 facing the cylinder 34. The diaphragm 36 is compressibly positioned between the valve cap interface 42 and the valve body interface 58 when the valve 30 is assembled and ready for use (as shown in FIGS. 3 to 5), such that the diaphragm 36 is positioned across the process ports 46. As more clearly shown in FIG. 8C, in an embodiment, the diaphragm 36 has a pre-formed deformation 78 which lays within the main recess 60 of the cylinder 34 when the valve 30 is assembled. The first surface 74 of the diaphragm 36 and the valve cap interface 42 of the valve cap 32 define a communication channel between the process ports 46.

In an embodiment (not shown) a circular projecting lip may extends from the valve cap interface 42 of the valve cap 32 and/or on valve body interface 58 to provide a supplemental pressure point between the first surface 74 of the diaphragm facing the valve cap 32 and/or the second surface 76 facing the cylinder 34. Such supplemental pressure point helps prevent the leak of process gas therebetween, for example in the case of overpressure of the process gas. One skilled in the art would understand that each one of the circular projecting lip is preferably located on the outskirt of the valve cap interface 42 and/or the body interface 58.

The diaphragm 36 can be made of a single layer of polymer or of multiple layers of polymer, with or without a thin metallic layer, or alternatively be made of metal only. For example, and without being limitative, metals that may be used are stainless steel 316, aluminum, chrome-nickel alloy, copper and the like. For applications requiring high gas-tightness sealing, a diaphragm 36 made of multiple layers of polymer is preferably used, while other applications require a thin metallic layer over the polymer layers.

Leak Collection

With additional reference to FIGS. 7C and 7D, in an embodiment, the cylinder 34 is provided with a leak collection system including a process purging channel 65 extending along the main recess 60, a process purging inlet passage 66 and a process purging outlet passage 68. The process purging inlet passage 66 is connected to an entry 67 of a purge line, and the process purging outlet passage 68 is connected to an exit 69 of the purge line. The cylinder 34 may be further provided with a pair of fluid inlets 70 and a pair of fluid outlets 72, the pair of fluid inlets 70 also being connected to the entry 67 of the purge line, and the pair of fluid outlets 72 being connected to the exit 69 of the purge line.

The cylinder 34 may also be provided with actuation purging/venting outlet passages 112 allowing a flow of fluid towards the actuation system 220, outside of the actuating mechanism 96. The difference in diameter between the purging/venting outlet passages 112 dictates the direction of the flow, the fluid moving from the purging/venting outlet passage 112 having a smaller diameter to the one having a larger diameter.

As seen in FIG. 6D, a purge circulation line may further include inner and outer annular channels 51 and 53 extending at the valve cap interface 42 of the valve cap 32. In the illustrated embodiment, the fluid inlets 70 and the fluid outlets 72 each have a first opening in the inner annular channel 51 and a second opening in the outer annular channel 53.

Figure 11:
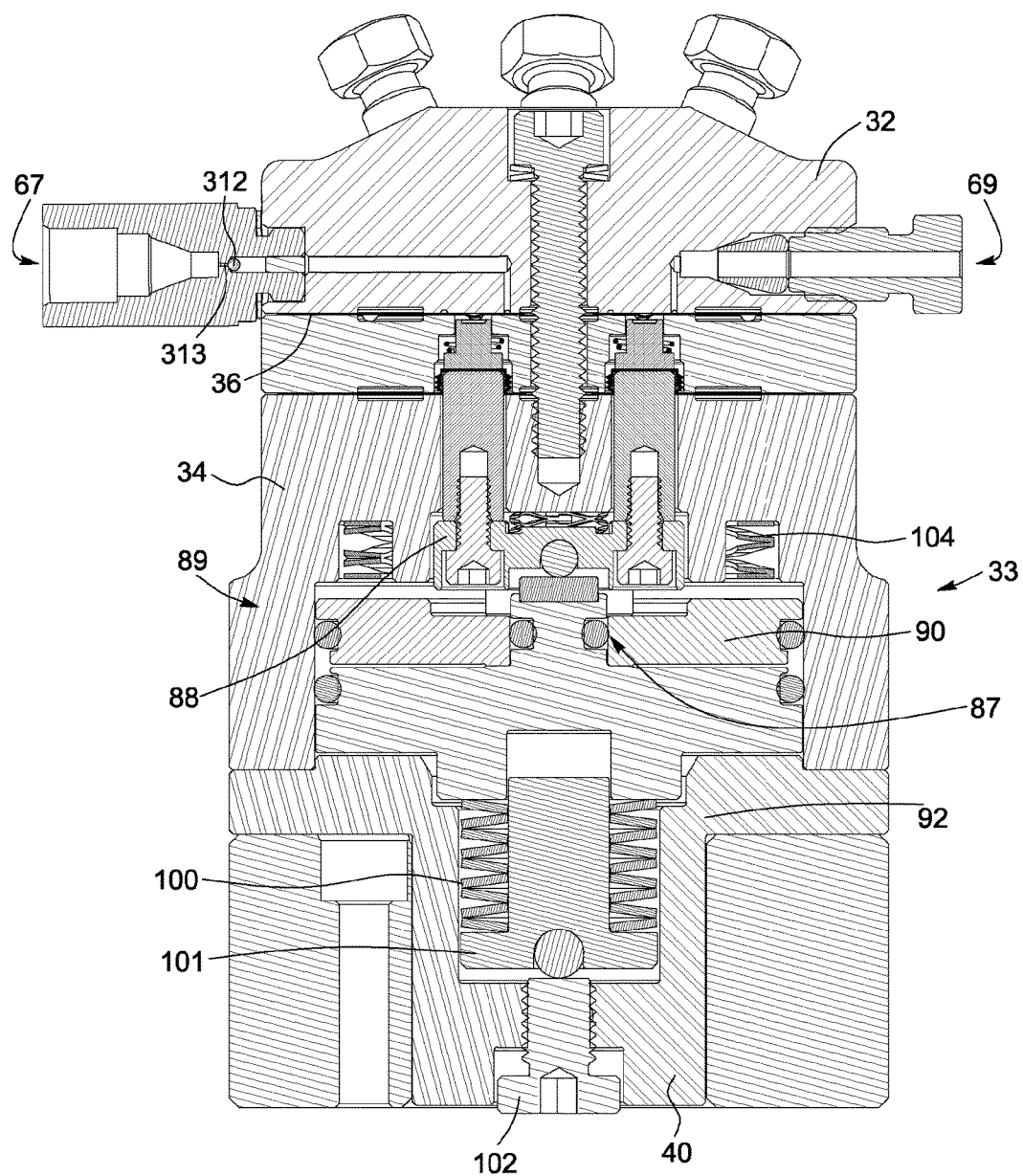
FIG. 11 is another cross-sectional side view of the diaphragm-sealed valve of FIG. 10.
Figure 12:
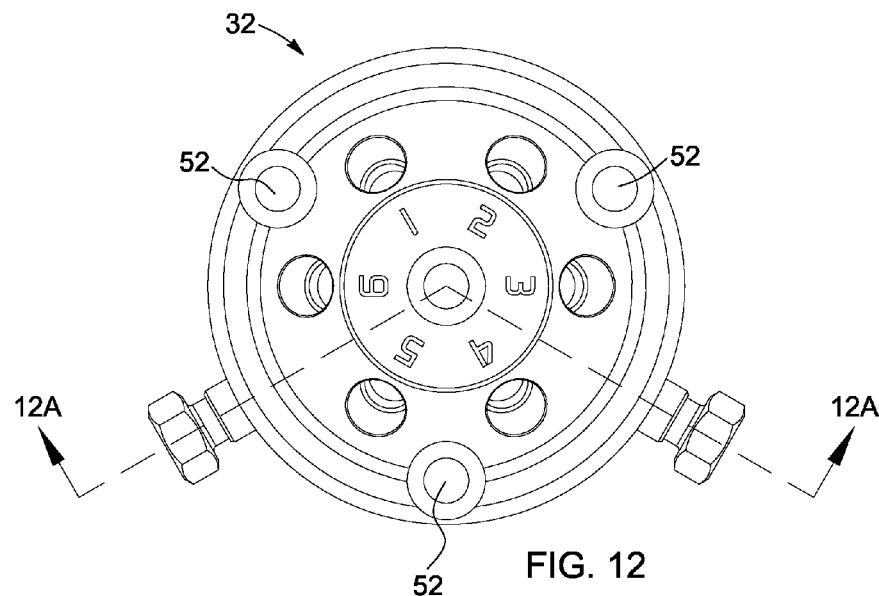
FIG. 12 is a top view of a valve cap according to an embodiment where a leak collection system is part of the valve cap.
Figure 12A:
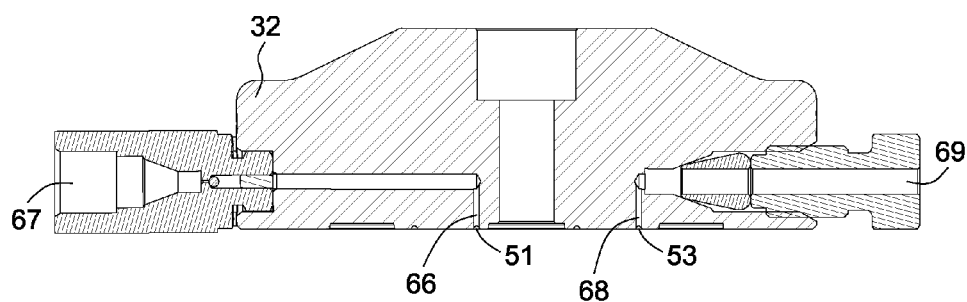
FIG. 12A is a cross-sectional side view of the valve cap of FIG. 12 taken along line 12A-12A.

Now referring to FIGS. 11 and 12A, in another embodiment, the leak collection system may be provided onto the valve cap 32 rather than onto the cylinder 34. Once again the leak collection system includes a process purging inlet passage 66 and a process purging outlet passage 68. The process purging inlet passage 66 has an opening in the inner annular channel 51 and is connected to an entry 67 of a purge line. The process purging outlet passage 68 has an opening in the outer annular channel 53 and is connected to an exit 69 of a purge line. In an embodiment, at least one connecting channel (not shown) is formed into the cylinder 34 to connect the inner annular channel 51 to the main recess 60 and at least one connecting channel (not shown) is formed into the cylinder 34 to connect the outer annular channel 51 to the main recess 60.

In an embodiment (not shown), the diameter of the purging outlet passage 68 and/or the diameter of the pair of fluid outlets 72 is greater than the diameter of the corresponding one of the process purging inlet passage 66 and the pair of fluid inlets 72 in order to prevent backflow of the purge gas flowing through the leak collection system.

The operation of a leak collection system is described in detail in the present Applicant's application PCT/CA2008/002138, which is incorporated herein by reference, and will not, as such, be described further herein.

Plungers

Now referring to FIGS. 4, 4A, 4E, 10 and 10A, the valve 30 is further provided with a plurality of plungers 82 for engaging and disengaging the diaphragm 36, in order to allow or prevent communication between adjacent ports. The plungers 82 are each positioned in one of the plunger passages 62 of the cylinder 34. In the context of the present document, the term "plunger" is understood to mean a mechanical component or assembly driven by or against a mechanical force or fluid pressure.

In the illustrated embodiment, each plunger 82 is formed of a base section 200 and a top section 202. The base section 200 preferably has a cylindrical shape ending in a head 201 which projects upward in the passage. The top section 202 preferably includes a diaphragm-engaging portion 215 and a foot 203. In the illustrated embodiment the base section 200 and top section 202 are not physically attached, but meet at an interface 205.

Still referring to FIGS. 4, 4A, 4E 10 and 10A, in the illustrated embodiment, each plunger passage 62 of the cylinder 34 of the valve body 33 comprises a shoulder 210. The plunger passage 62 therefore has a narrower portion 207 between the shoulder 210 and the valve body interface 58 of the cylinder 34. In order to adapt to such shoulder 210, the top section 202 of each plunger 82 is sized and shaped such that the diaphragm-engaging portion 215, which is located opposite to the foot 203 of the top section 202, is movable within the narrower portion 207 defined by the shoulder 210. The diaphragm-engaging portion 215 is therefore itself narrower than the foot 203 of the corresponding top section 202, which results in the foot 203 of the corresponding top section 202 being movable in the plunger passage 62, but being too large to enter the narrower portion 207.

A biasing mechanism is provided between the shoulder 210 and the foot 203 of the top section 202, for biasing the top section 202 of each plunger 82 away from the diaphragm 36, when no pressure is exerted on the top section 202 by the base section 200. For example and without being limitative, the biasing mechanism can be a spring 212 surrounding a section of the diaphragm-engaging portion 215. The spring 212 abuts on the top surface of the foot 203 and the bottom surface of the shoulder 210, thereby biasing the top section 202 downwards.

One skilled in the art will understand that, in an alternative embodiment, the above described plunger configuration could work properly without the shoulder 210, as long as a biasing mechanism is provided to bias the top section 202 of each plunger 82 away from the diaphragm 36 when not pressured by the corresponding base section 200.

It will be further understood that the plunger construction illustrated in the enclosed figures and described above are provided by way of example only and that, in an alternative embodiment the plungers may be of a different design, for example such as shown in patent applications nos. PCT/CA2008/001276, PCT/CA2009/001250 or PCT/CA2010/000513.

When the valve is activated, the plungers 82 can slide in the corresponding passage 62, between a closed position and an open position. For example, in FIG. 4E the right side plunger is shown in the closed position, whereas the left side plunger is shown in the open position.

In the closed position, the plunger 82 engages the diaphragm 36 between two adjacent ports, and therefore interrupts the communication between these ports. Engagement of the diaphragm 36 is effected by the base section 200 of a plunger 82 being moved upward and pressing against the top section 202. The pressure exerted by the base section 200 counteracts the biasing mechanism, for example by compressing the spring 212. Therefore, the top section 202 is brought upward, and the diaphragm-engaging portion 215 engages the diaphragm 36.

In the open position, the plunger 82 is disengaged from the diaphragm 36 and therefore allows the communication between the two adjacent ports. The open position is reached when the base section 200 slides downward and away from the top section 202. When none or insufficient pressure is exerted on the top section 202 by the bottom section 200, the biasing mechanism acts to bias the top section 202 away from the diaphragm 36 in order to allow communication between the two adjacent ports.

In other embodiments the plungers may interact with the ports in a different manner without departing from the scope of the invention. For example, the plungers may be used to block the ports directly, in a valve as shown in PCT/CA2005/000236.

In the illustrated embodiment, both the bottom section 200 and top section 202 of the plungers 82 are cylindrical.

However one skilled in the art will understand that, in an alternative embodiment, the bottom section 200 and top section 202 may take other shapes than that of a cylinder, as long as they can result in the above-described open and closed positions.

The separation between the head 201 of the base section 200 and the foot 203 of the top section 202 of each plunger 82 results in the diaphragm engaging section 215 of the top section 202 of the plunger 82 contacting the diaphragm 36 perpendicularly, for example, even when the base section 200 of the plunger 82 is not perfectly perpendicular with the valve body interface 58 of the cylinder 34 or if the base sections 200 of the plungers 82 are not perfectly aligned with the top sections 202 of the plungers 82. Furthermore, if for any reason, the support structures (which will be described below) are not perfectly parallel with the valve body interface 58 of the cylinder 34, or if the alignment of the valve cap 32 with the cylinder 34 is not perfectly tuned, the top sections 202 of the plungers 82 will remain perpendicular with the valve body interface 58 of the cylinder 34 when a support structure is forced up by the action of the actuation gas, as will be described below.

One skilled in the art will understand that even though the separation between the head 201 of the base section 200 and the foot 203 of the top section 202 of each plunger 82 offers several advantages, as stated above, in an alternative embodiment the plungers 82 may present a single unitary section.

Actuation System

In order for the plungers 82 to be movable between the open and closed positions, the base section 200 of each plunger 82 is connected to an actuation system 220. The base section 200 is connected to the actuation system 220 by a mounting component 83 such that the head 201 of each base section 200 projects away therefrom. For example and without being limitative, a screw can be used to mount the base section 200 of the plunger 82 to the actuation system 220.

As mentioned above, one skilled in the art will understand that even though the actuation system described herein refers to an embodiment where the plungers 82 include a base section 200 and a top section 202, in an embodiment, the actuation system 220 may be used in combination with plungers presenting a single unitary section.

As better seen in FIG. 3, in an embodiment, the actuation system 220 includes a first support structure 87 comprising a push plate 88 and a first piston 92 as well as a second support structure 89 comprising a second piston 90. As illustrated, the first piston 92 is located below the second piston 90 and extends therethrough and for simplicity these two pistons will hereinafter be referred to as the lower piston 92 and the upper piston 90, respectively.

In the illustrated embodiment, each plunger 82 is either normally closed or normally opened. The base sections 200 of the normally closed plungers are mounted to the push plate 88 and the base sections 200 of the normally open plungers are mounted to the upper piston 90.

The push plate 88 extends within the cavity 63 of the cylinder 34, substantially parallel to the valve body interface 58 of the cylinder 34, i.e. substantially perpendicular to the plunger passages 62 and a central axis of the cylinder 34. The push plate 88 is movable transversally to the valve body interface 58, or, in other words, substantially in parallel to the central axis of the cylinder 34. The bottom sections 200 of the normally closed plungers 82 are mounted to the push plate 88. A plurality of channels extend across the push plate 88 for allowing the bottom sections 200 of the normally open plungers 82 to move therethrough. The upper piston 90 extends contiguously under the push plate 88, the bottom sections 200 of the normally open plungers 82 being mounted to it. The lower piston 92 extends under the upper piston 90 contiguously to it and an upper section 93 extends through a central aperture 91 in the upper piston 90 such that a top section 240 of the lower piston 92 can engage the push plate 88.

Figure 3A:
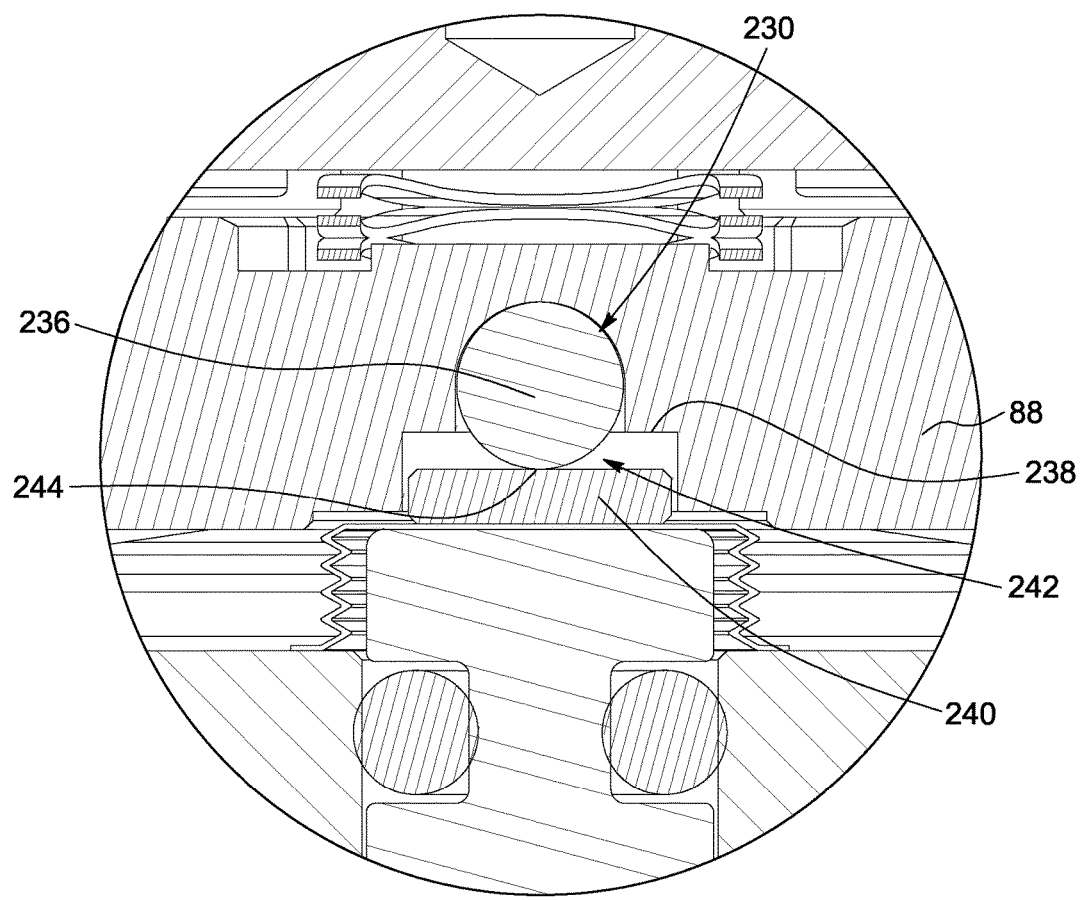
FIG. 3A is an enlarged view of section 3A of FIG. 3.

As can be seen in FIGS. 3 and 3A, in an embodiment the push plate 88 is provided with a bearing receiving section 230 centered between its right side extremity 232 and left side extremity 234. The bearing receiving section 230 is located in a bottom wall 238 of the push plate 88, thereby forming a downward extending cavity. The cavity formed by the bearing receiving section 230 is sized and shaped for receiving therein a first portion of a bearing 236. It should be understood that in the present document, the term "bearing" is used to refer to any spherical body or ball made of hardened material and having a smooth surface in order to provide rolling abutment between adjacent surfaces. A second portion of the bearing 236 projects downwardly, away from the bottom wall 238. This second portion is referred to as the projecting portion 242. The size of the bearing 236 may be such that the first portion closely matches the inside of the bearing receiving section 230, thereby preventing any looseness between the two components, while allowing the bearing 236 to roll freely therein. The lower piston 92 engages the push plate 88 at a single tangential contact point 244 between the bearing 236 and a top section 240 of the lower piston 92. The tangential contact point 244 is provided by the rounded configuration of the bearing 236 and the flat configuration of the top section 240 of the lower piston 92, and allows a rolling abutment between the lower piston 92 and the push plate 88. Such a configuration prevents a misalignment of the push plate 88 within the cavity 63 of the cylinder 34, which would result in a misalignment of the plungers 82, by allowing the push plate 88 to automatically be re-centered when the plungers 82 are pushed against the diaphragm 36.

In the illustrated embodiment, the top section 240 of the lower piston 92 is a separate part made of a hardened material such as, without being limitative, stainless steel 17-4 PH, in order to provide a high hardness material at the contact point. However, in an embodiment the top section 240 could also be integral with the lower piston 92.

One skilled in the art will understand that even though the presence of the above-described bearing between the top section 240 of the lower piston 92 and the push plate 88 presents several advantages, in an alternative embodiment, the top section 240 of the lower piston 92 may engage the push plate 88 directly, without the use of the above-described bearing assembly.

In the illustrated embodiment, when either the upper piston 90 or the lower piston 92 are retracted, the corresponding bottom sections 200 of the plungers 82 attached thereto are pulled downward, resulting in a release of the pressure exerted on the top sections 202.

As can be seen in FIG. 3, biasing mechanisms are provided such that the lower piston 92 is upwardly biased and that the upper piston 90 is downwardly biased. In an embodiment, a Belleville washer support 101 and a Belleville washer assembly 100 cooperate to bias the lower piston 92 upwardly. A bottom cap load screw 102 may be provided to control an upward force on the Belleville washer support 101. Still according to an embodiment, a wave spring 104 extending over the upper piston 90 exerts a downward force on the upper piston 90 and therefore downwardly biases the upper piston 90. One skilled in the art will understand that, in alternative embodiments, different biasing assembly may be provided for biasing the lower piston 92 upwardly and the upper piston 90 downwardly.

To actuate the plungers, an actuating mechanism 96 is provided to control a distance or space between the upper piston 90 and the lower piston 92. In this embodiment, it can be seen that the actuating mechanism 96 actuates the plungers 82 between the open and closed positions, for example by injection of an actuation gas between the upper piston 90 and the lower piston 92, the actuating mechanism 96 being pneumatic actuators.

Figure 3B:
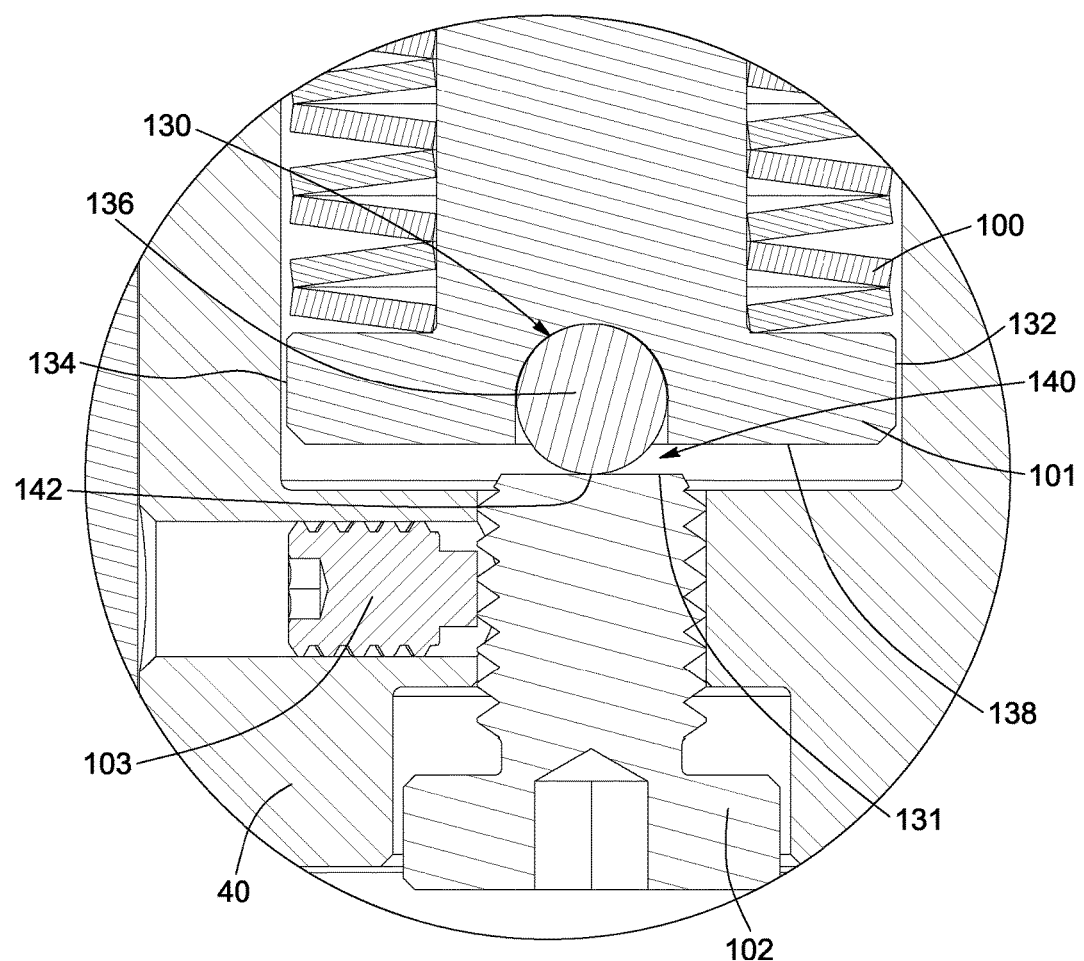
FIG. 3B is an enlarged view of section 3B of FIG. 3.

As can be seen in FIGS. 3 and 3B, in an embodiment, the bottom cap 40 is affixed to the cylinder 34, preferably with socket head cap screws. In the illustrated embodiment, the bottom cap also houses the bottom cap load screw 102 that allows adjustment of the pressure exerted on the lower piston 92 via the Belleville washer support 101 and Belleville washer assembly 100. To facilitate the alignment of the actuation system 220 subsequent to the pressure exerted by the bottom cap load screw 102 on the Belleville washer support 101, the Belleville washer support 101 may be provided with a bearing receiving section 130 centered horizontally between its right side extremity 132 and left side extremity 134. The bearing receiving section 130 is located on a bottom wall 138 of the Belleville washer support 101 and forms a downward extending cavity. The cavity formed by the bearing receiving section 130 is sized and shaped for receiving therein a first portion of a bearing 136. A second portion of the bearing 136 projects downwardly away from the bottom wall 138 of the Belleville washer support 101. This second portion is referred to as the projecting portion 140. The size of the bearing 136 is such that it closely matches the inside of the bearing receiving section 130, thereby preventing any looseness between the bearing 136 and the bearing receiving section 130, while allowing the bearing 136 to roll freely therein. The bottom cap load screw 102 engages the Belleville washer support 101 at a single tangential contact point 142 between the bearing 136 and a top section 131 of the bottom cap load screw 102. The tangential contact 142 is provided by the rounded configuration of the bearing 136 and the flat configuration of the top section 131 of the bottom cap load screw 102. The single tangential contact point 142 prevents a misalignment of the actuation system resulting from the bottom cap load screw 102 exerting an off-centered pressure on the Belleville washer support 101, which in turn would cause a misalignment of the lower piston 92. Such an off-centered pressure of the bottom cap load screw 102 on the Belleville washer support 101 can be encountered in prior art valves, since the locking screw 103 used for locking the bottom cap load screw 102 in place tends to shift the position of the bottom cap load screw 102 from its centered position.

One skilled in the art will understand that even though the presence of the above-described bearing between the top section 131 of the bottom cap load screw 102 and the Belleville washer support 101 presents several advantages, in an alternative embodiment, the top section 131 of the bottom cap load screw 102 may engage the Belleville washer support directly, without the use of the above-described bearing assembly.

In an embodiment and as can be seen in FIGS. 4 and 10, the bottom cap 40 can also be provided with a bottom cap actuation vent 114 extending in it and located opposite to the actuating mechanism 96, for preventing pressure build up between the lower piston 92 and the bottom cap 40.

The operation of such an actuation vent 114 is described in detail in the present Applicant's application PCT/CA2009/001783 which is incorporated herein by reference, and will not, as such, be described further herein.

One skilled in the art will easily understand that even though an actuation system according to an embodiment is described herein, in alternative embodiments, other actuation system resulting in the movement of the plungers between a closed and an open position could be used.

Sealing Assembly

In order to block leaked gas from the diaphragm 36, in an embodiment a sealing assembly 300 is provided in the cylinder 34 of the valve body 33. In the undesirable eventuality of a leak of gas through the diaphragm 36, the sealing assembly 300 is configured to prevent the gas leaked through the diaphragm 36 from leaking out of the valve 30 or into the actuating mechanism 96 of the actuation system 220. As will be described below, the sealing assembly 300 is configured to contain the gas and ensure that any gas that may leak through the diaphragm is discharged via the exit 69 of the purge line.

Referring to FIGS. 10, 10A, 14A and 14B, in an embodiment the sealing assembly 300 includes a sealing diaphragm 303 for sealing each one of the plunger passages 62 at an interface between the upper section 34a and the lower section 34b of the cylinder 34 of the valve body 33. In other words, the sealing diaphragm 303 is configured to prevent any gas that may leak through the diaphragm 36 to flow through the plunger passages 62.

Figure 10A:
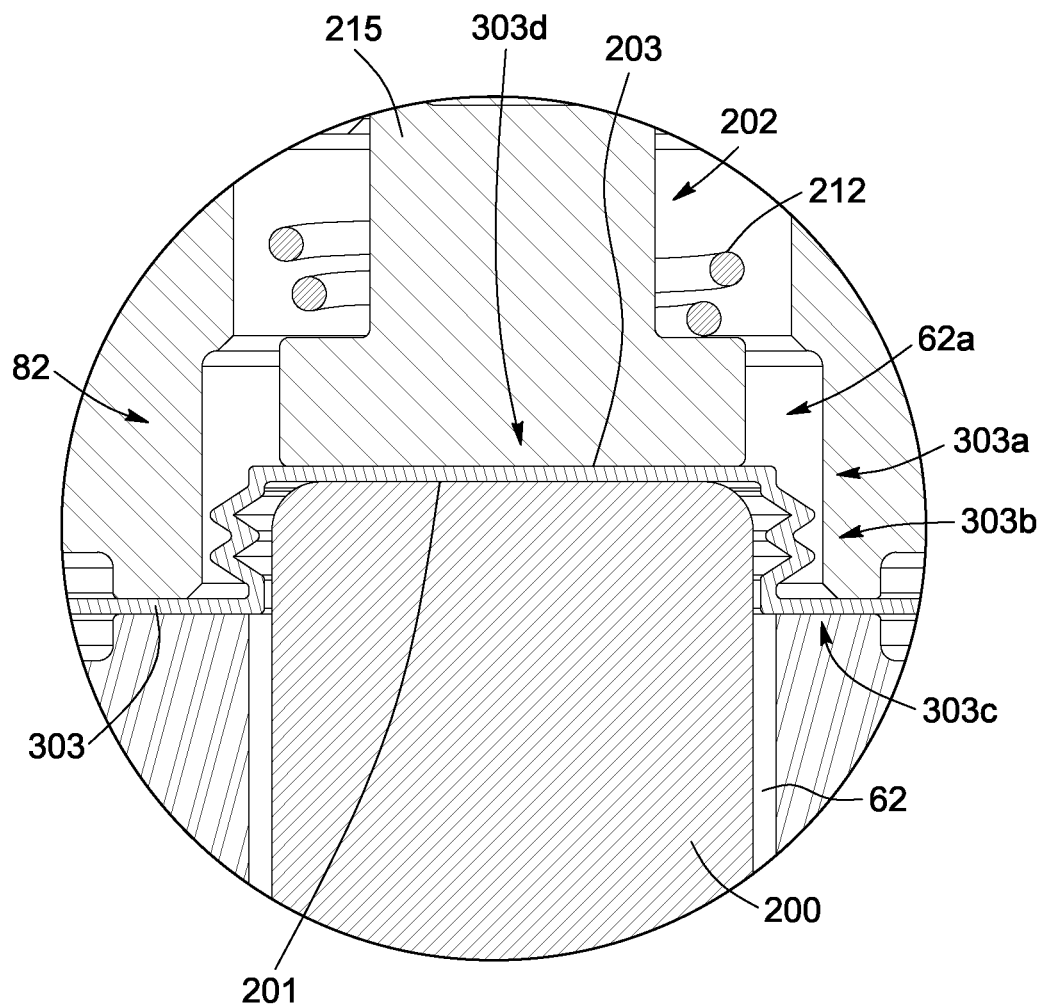
FIG. 10A is an enlarged view of section 10A of FIG. 10.

As can be seen, in the illustrated embodiment, the sealing diaphragm 303 is positioned between the upper section 34a of the cylinder 34 and the lower section 34b of the cylinder 34 and is shaped so as to form a plurality of passage seals 303a. As best seen in FIG. 10A, each one of the plurality of passage seals 303a is circular and extends into a corresponding plunger passage 62 to cover the base sections 200 of a corresponding plunger 82. More specifically, each one of the plurality of passage seals 303a seals a corresponding plunger passage 62 at the interface between the upper section 34a of the cylinder and the lower section 34b, as the passage seal 303a extends between the base sections 200 and the top section 202 of the corresponding plunger 82. Each one of the plurality of passage seals 303a includes a bellows section 303b between the peripheral base 303c and the top section 303d. As will be seen from FIGS. 10 and 10A, in an embodiment, each plunger passage 62 includes an enlarged portion 62a around the top of the base section 200 of the corresponding plunger 82. One skilled in the art would understand that, in alternative embodiments, other configurations allowing each one of the plurality of passage seal 303a to expand and retract according to the movement of the base sections 200 of the corresponding plunger 82 could also be used.

Advantageously, each one of the above described passage seal 303a cooperates with the corresponding biasing mechanism to help in biasing the top section 202 of the corresponding plunger 82 downwards, by biasing the base sections 200 downwardly. In other words, when a plunger 82 is moved between a closed configuration and an open configuration, the passage seal 303a will help biasing the base sections 200 of the plunger 82 downward, the passage seal 303a being extended when the plunger 82 is configured in the closed configuration.

In an embodiment the sealing diaphragm 303 is a metallic diaphragm. For example and without being limitative, the sealing diaphragm 303 may be made of stainless steel 316, aluminum, chrome-nickel alloy, copper and the like. Moreover, in an embodiment the sealing diaphragm 303 can be provided with a protective coating for increasing its resistance against gases that that may leak through the diaphragm 36, thereby providing an increased resistance to prevent or delay the leak of gas therethrough. For example and without being limitative, the sealing diaphragm 303 may be coated with polytetrafluoroethylene or the like.

One skilled in the art will understand that, in an alternative embodiment, a sealing assembly 300 similar to the above described sealing diaphragm 303 may be provided where each passage seal 303a is independent from one another. In such an embodiment, each passage seal 303a sealing a corresponding plunger passage 62 would include a peripheral end being pressed between the upper section 34a of the cylinder 34 and the lower section 34b and would extend between the base sections 200 and the top section 202 of the corresponding plunger 82, as described above.

Referring to FIGS. 4 to 4D', in an alternative embodiment, the sealing assembly 300 includes a first seal 302 for sealing an interface between the upper piston 90 and the cylinder 34 of the valve body 33, a second seal 304 for sealing an interface between the upper piston 90 and the lower piston 92 and a plurality of third seals 306 for sealing the connection between the upper piston 92 and each one of the plungers 82 mounted thereto.

In an embodiment, the first seal 302 is a circular seal located in the periphery of the upper piston 90 of the actuation system 220. The first seal 302 is configured to prevent any gas that may leak through the diaphragm 36 to flow between the upper piston 90 and the cylinder 34 of the valve body 33. In the illustrated embodiment, the first seal 302 is connected at a first end 302a to the upper piston 90 and at a second end 302b to the cylinder 34 of the valve body 33. In an embodiment, the first end 302a of the first seal 302 is connected to the upper piston 90 by brazing. However, one skilled in the art will understand that, in alternative embodiments, other joining process resulting in a sealed connection therebetween may be used. In the illustrated embodiment, the second end 302b of the first seal 302 is connected to the cylinder 34 of the body 33 by being pressed between the upper section 34a of the cylinder 34 and the lower section 34b of the cylinder 34. As previously mentioned, in an embodiment, the pressure between the upper section 34a of the cylinder 34 and the lower section 34b of the cylinder 34 may be controlled via the cylinder body screws 35. In an embodiment a circular projecting lip 308 may be provided on the lower wall 341 of the upper section 34a and/or on the upper wall 342 of the lower section 34b of the cylinder 34 to provide a supplemental pressure point on the second end 302b of the first seal 302 and thereby further ensure a proper sealing therebetween. One skilled in the art will understand that other joining process resulting in a sealed connection between the second end 302b of the first seal 302 and the cylinder 34 may be used. In order to allow the first seal 302 to expand and retract according to the movement of the upper piston 90, in an embodiment the first seal 302 may include a bellows section 302c between the first end 302a and the second end 302b. One skilled in the art would understand that, in alternative embodiments, other configurations allowing the first seal 302 to expand and retract according to the movement of the upper piston 90 could also be used.

In an embodiment, the second seal 304 covers the central aperture 91 of the upper piston 90 through which the upper section 93 of the lower piston 92 extends. The second seal 304 is configured to prevent any gas that may leak through the diaphragm 36 to flow between the upper piston 90 and the upper section 93 of the lower piston 92 extending therethrough. In the illustrated embodiment, the second seal 304 has a rounded configuration but one skilled in the art will understand that, in alternative embodiments, other configurations could be provided. The outer periphery 304a of the second seal 304 is connected to the upper piston 90, such as to seal the central aperture 91 of the upper piston 90 into which the upper section 93 of the lower piston 92 extends. In an embodiment, the periphery 304a of the second seal 304 is connected to the upper piston 90 by brazing. However, one skilled in the art will understand that, in alternative embodiments, other joining process resulting in a sealed connection between the upper piston 90 and the periphery 304a of the second seal 304 may be used. The second seal 304 extends upwardly such as to cover the upper section 93 of the lower piston 92 extending through the upper piston 90. In the illustrated embodiment, the top extremity 304b of the second seal 304 extends between the upper section 93 of the lower piston 92 and the top section 240 of the lower piston 92. In order to allow the second seal 304 to expand and retract according to the movement of the upper section 93 of the lower piston 92, in an embodiment, the second seal 304 includes a bellows section 304c between the outer periphery 304a and the top extremity 304b. Once again, one skilled in the art would understand that other configurations allowing the second seal 304 to expand and retract according to the movement of the upper section 93 of the lower piston 92 could also be used.

In an embodiment, each one of the plurality of third seals 306 is a bushing, a washer, a shim or the like, configured to prevent gas that may leak through the diaphragm 36 to leak between the upper piston 90 and the normally open plungers 82 mounted thereto. A third seal 306 is provided for each one of the normally open plungers 82 mounted to the upper piston 90. In an embodiment each one of the third seals 306 is provided between the upper piston 90 and the head of the mounting component 83 for mounting the normally open plunger 82 thereto. In an embodiment, a circular projecting lip 310 may be provided on the corresponding section of the upper piston 90 and/or on the head of the mounting component 83 to provide a supplemental pressure point on the third seal 306 and thereby further ensure a proper sealing therebetween.

In an embodiment each one of the first seal 302, the second seal 304 and the plurality of third seals 306 are metallic seals. For example and without being limitative, the seals may be made of stainless steel 316, aluminum, chrome-nickel alloy, copper and the like. Moreover, in an embodiment the first seal 302, the second seal 304 and/or the plurality of third seals 306 can be provided with a protective coating for increasing the resistance of the seals against gases that that may leak through the diaphragm 36, thereby providing an increased resistance to prevent or delay the leak of gas through the seals. For example and without being limitative, the first seal 302, the second seal 304 and/or the plurality of third seals 306 may be coated with polytetrafluoroethylene or the like.

As will be understood, in the event of a leakage of gas through the diaphragm 36, the above described sealing assemblies 300 result in the gas being contained in a specific region of the process assembly 301, outside of the actuating mechanism 96 of the actuation system 220.

In the absence of the sealing assembly 300, the gas might flow through different flow paths subsequently to a leak through the diaphragm 36. In the case where the gas is corrosive, toxic, unstable and/or reactive, many of the possible flow paths are undesirable as they may lead to damage to the valve 30, the instrument onto which the valve 30 is installed or to auxiliary equipment used to control the valve 30. Moreover, the flow of the leaked gas in different flow paths makes it difficult to detect promptly the occurrence of a leak through the diaphragm and to consequently promptly initiate desirable actions, such as the shutting of the gas supply to the valve.

Figure 9:
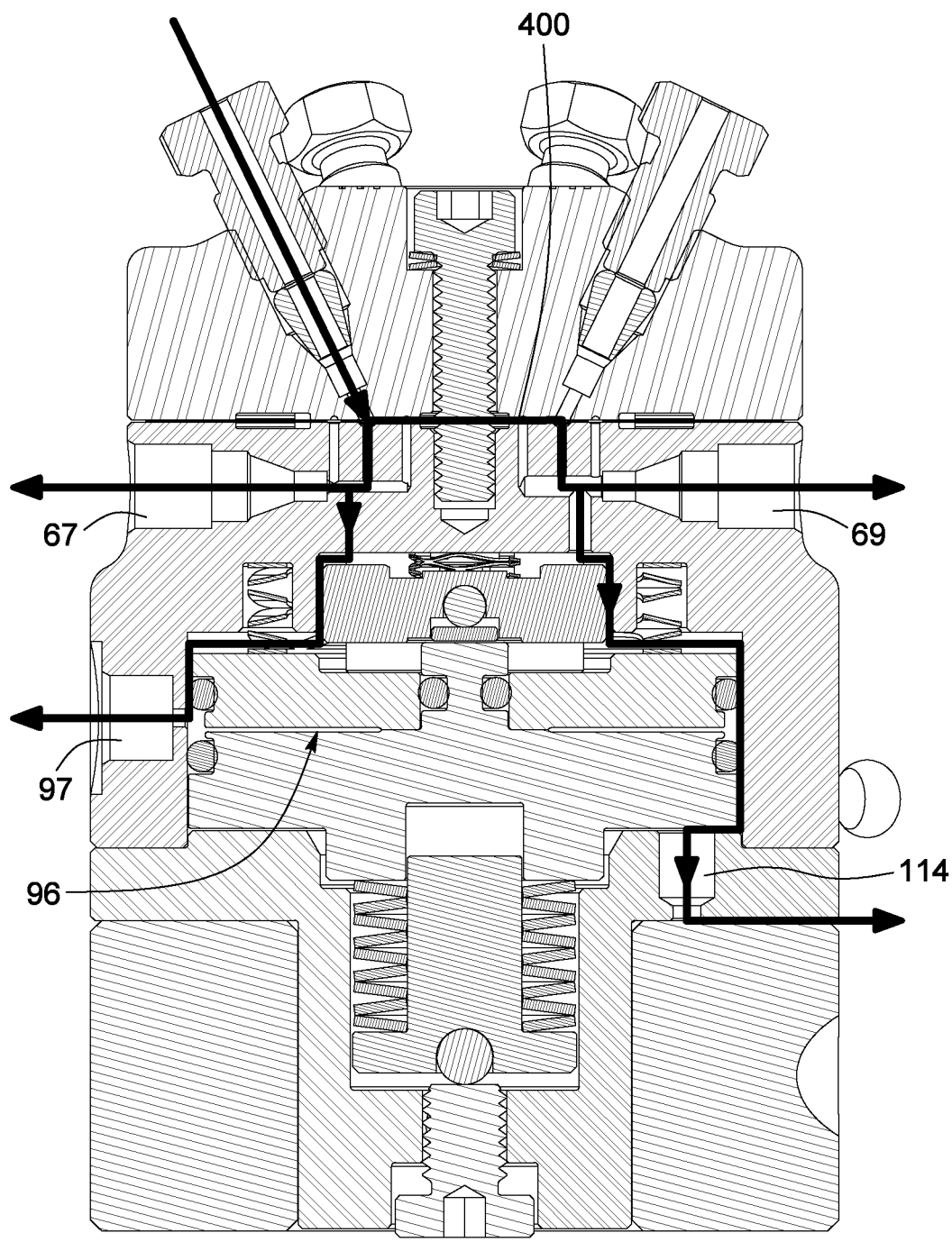
FIG. 9 (PRIOR ART) is a cross-sectional side view of a diaphragm-sealed valve, according to an embodiment, and including a schematic representation of the flow path of a gas subsequently to a leak through the diaphragm when no sealing assembly is provided in the valve body.
Figure 13:
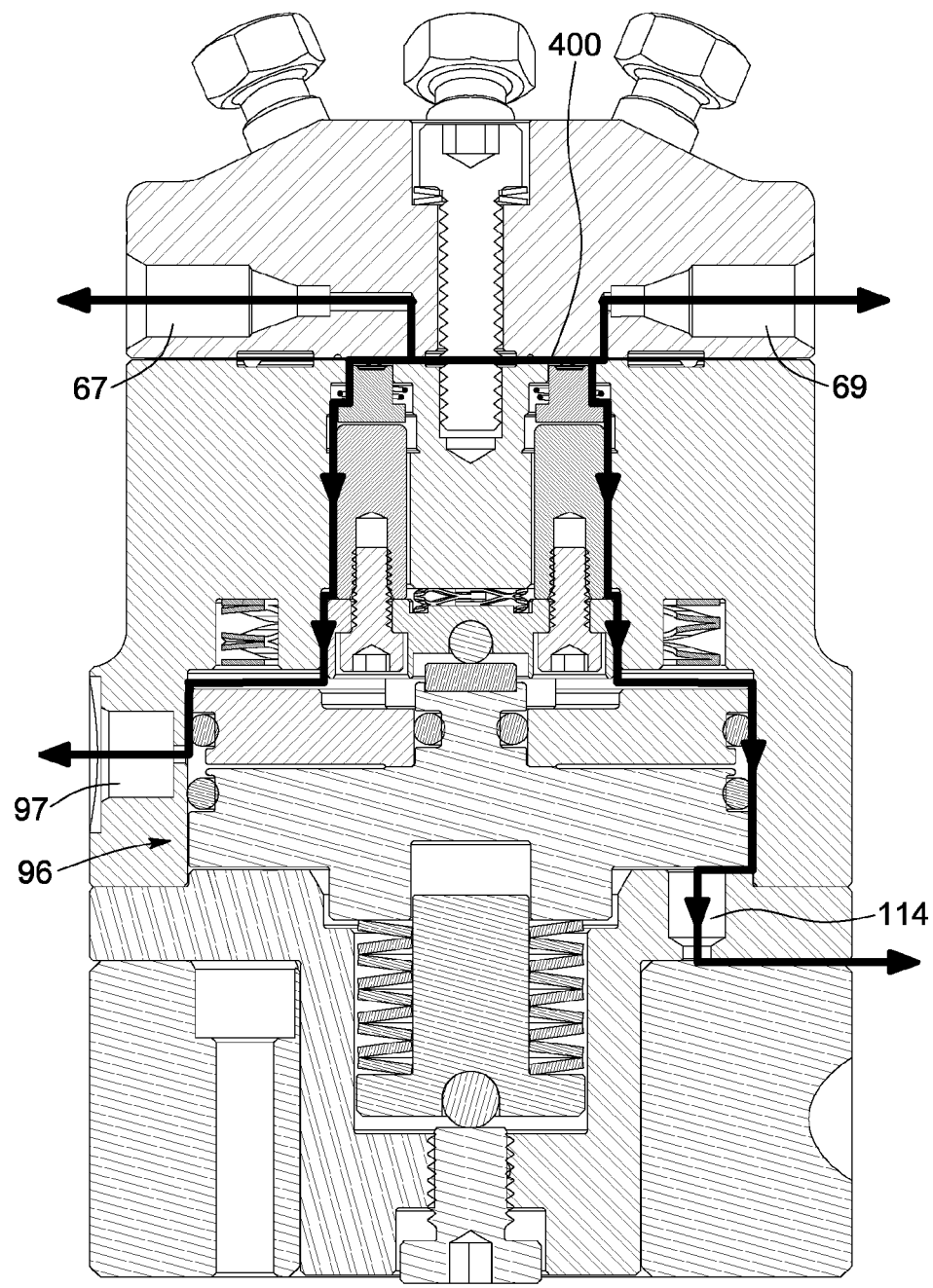
FIG. 13 (PRIOR ART) is a cross-sectional side view of a diaphragm-sealed valve, according to an embodiment, and including a schematic representation of the flow path of a gas subsequently to a leak through the diaphragm when no sealing assembly is provided in the valve body.

For example, as shown in FIGS. 9 and 13 (PRIOR ART), without the above described sealing assembly, subsequently to a leak through the diaphragm, the possible flow path 400 of the gas comprises a flow into the actuating mechanism 96 of the actuation system and subsequently upstream to an actuation gas source via the actuation inlet 97 or into the outer environment through the actuation vent 114. The flow path 400 also includes upstream to the purge gas source via the entry 67 of the purge line or downstream to a safe purge gas vent area through the exit 69 of the purge line. In the above described possible flow path 400, the possible gas flow into the actuating mechanism 96 of the actuation system and subsequently upstream to an actuation gas source via the actuation inlet 97 or into the outer environment through the actuation vent 114 are the paths that are most likely to cause damage, and are therefore undesirable. A flow of gas upstream to the purge gas source via the entry 67 of the purge line is also undesirable but can be avoided using a check valve 312, as will be described below and as can be seen, for example, in FIGS. 5 and 11.

Figure 9A:
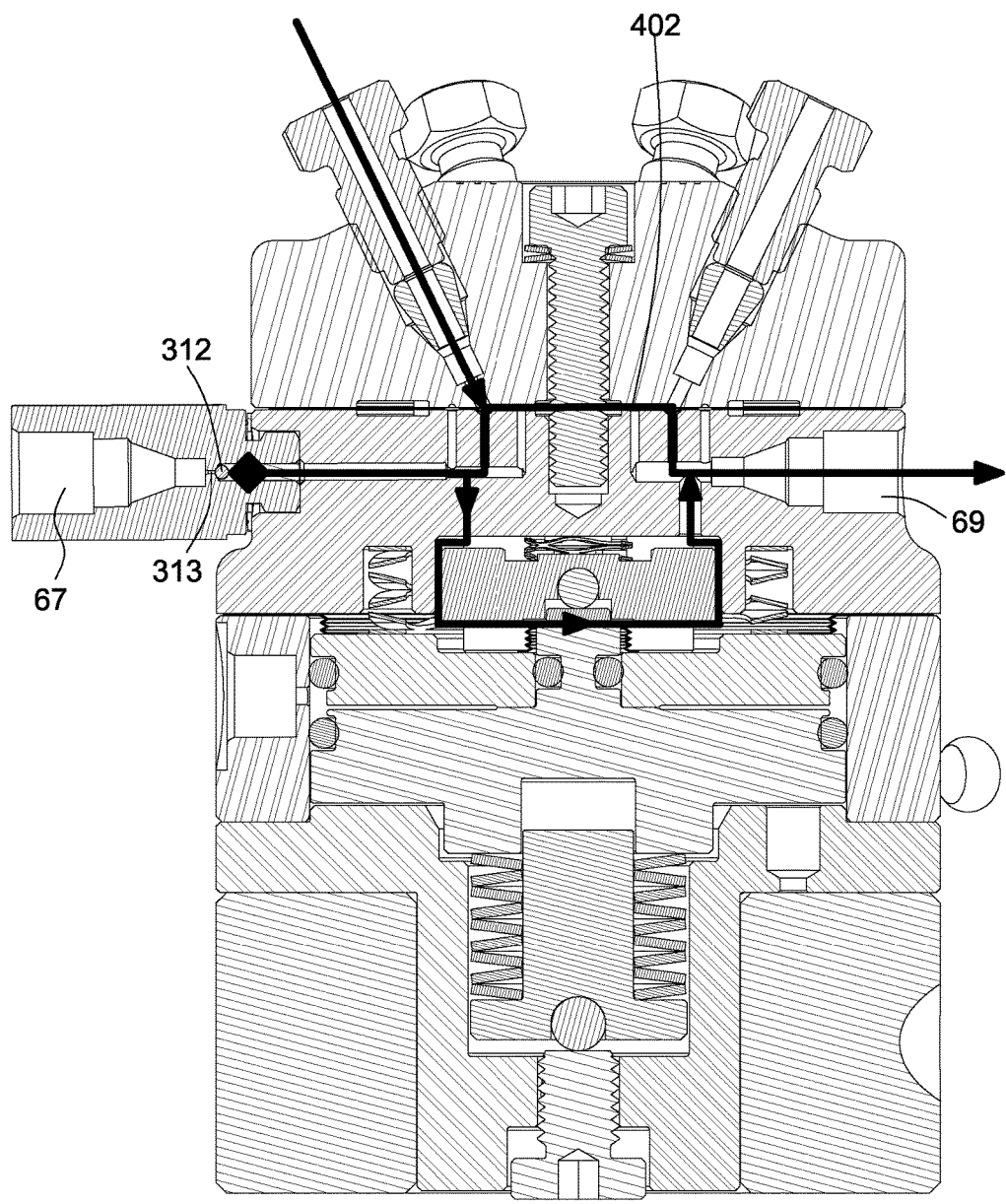
FIG. 9A is a cross-sectional side view of a diaphragm-sealed valve, according to an embodiment, and including a schematic representation of the flow path of a gas subsequently to a leak through the diaphragm when a sealing assembly is provided in the valve body.
Figure 13A:
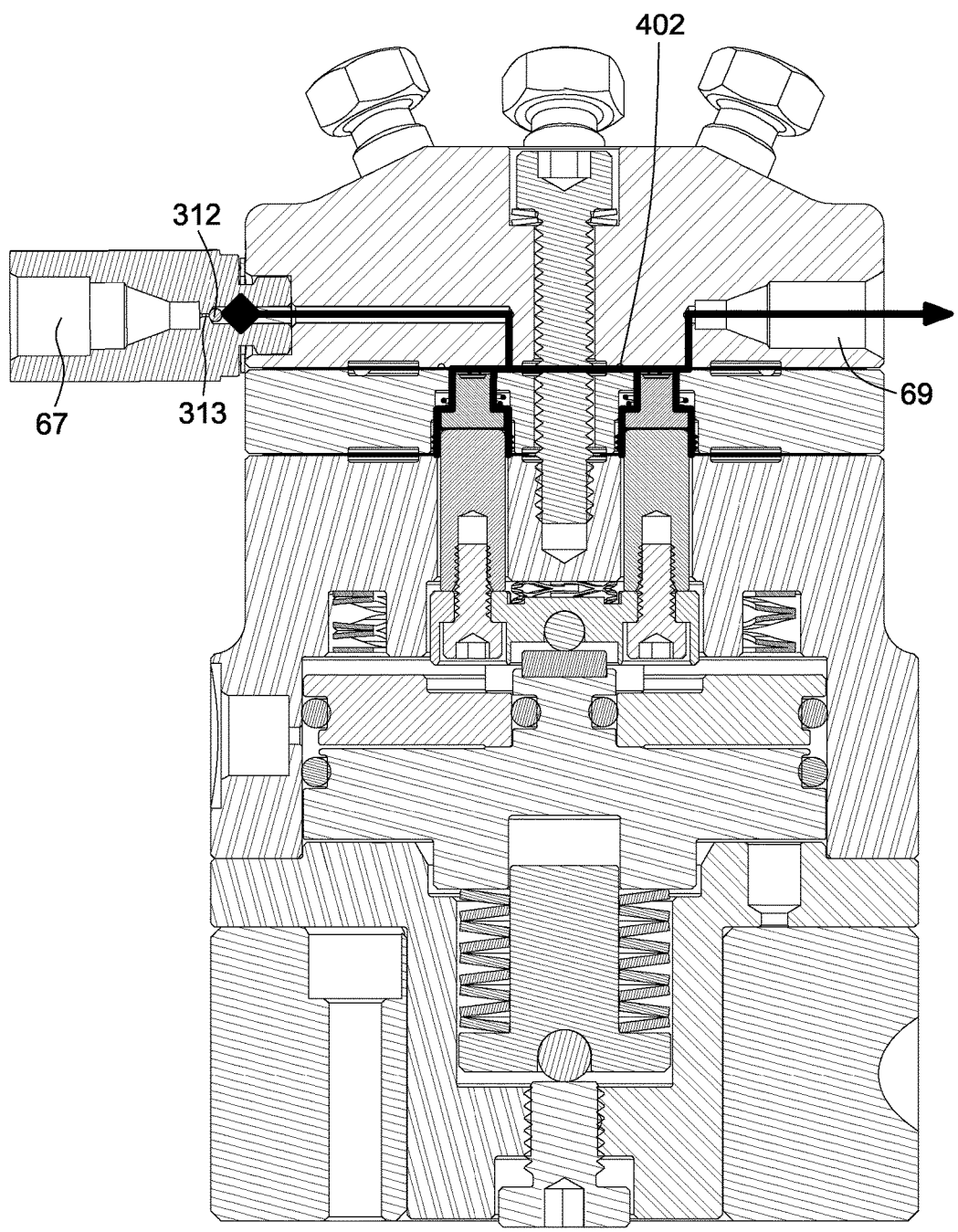
FIG. 13A is a cross-sectional side view of a diaphragm-sealed valve, according to an embodiment, and including a schematic representation of the flow path of a gas subsequently to a leak through the diaphragm when a sealing assembly is provided in the valve body.
Figure 14A:
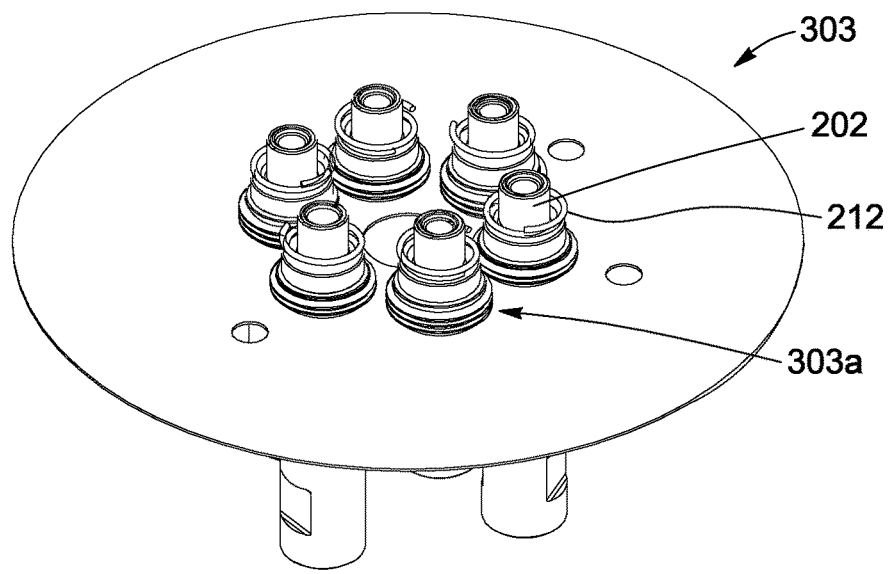
FIG. 14A is a perspective top view of a sealing diaphragm and the top section of the plungers according to an embodiment.
Figure 14B:
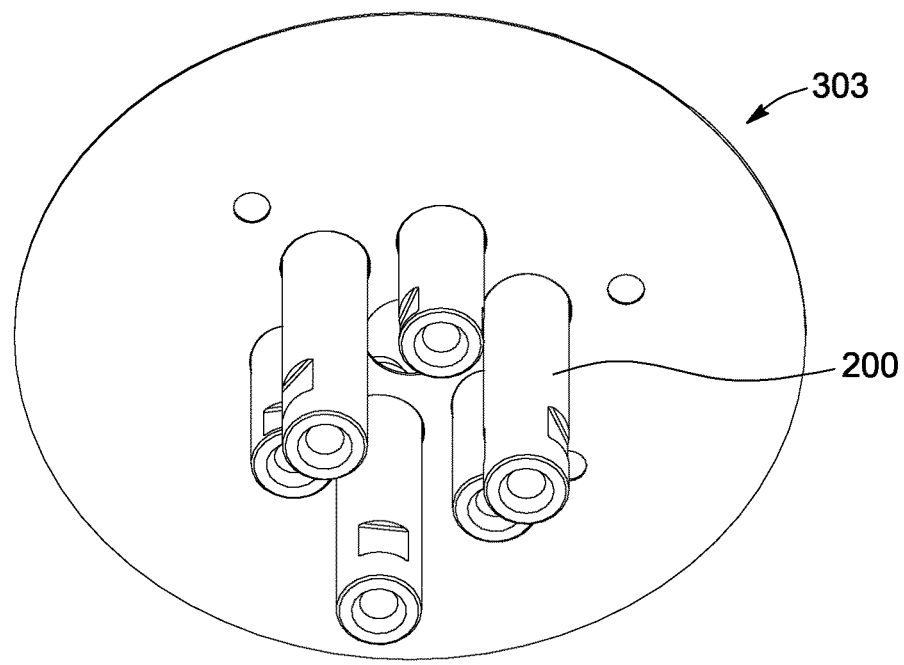
FIG. 14B is a perspective bottom view of a sealing diaphragm and the bottom section of the plungers according to an embodiment.

Referring to FIGS. 9A and 13A, when a sealing assembly 300 is provided, the only available flow path 402 for a gas, subsequently to a leak through the diaphragm, is upstream to the purge gas source via the entry 67 of the purge line or downstream to a safe purge gas vent area through the exit 69 of the purge line. Given that a flow of gas upstream to the purge gas source via the entry 67 of the purge line is undesirable, in an embodiment and as can be seen in FIGS. 9A and 13A, the entry 67 of the purge line is provided with a check valve 312 which allows the purge gas to flow in a first entry direction but prevents upstream gas flow via the entry 67 of the purge line in a second opposite exit direction. Therefore, the combination of the check valve 312 in the entry 67 of the purge line and the sealing assembly 300 results in the only flow path 402 for gas leaking through the diaphragm 36 being downstream to a safe purge gas vent area via the exit 69 of the purge line. Such a configuration thereby allows the monitoring of the purge gas flowing through the exit 69 of the purge line in order to promptly detect a variation therein that may be indicative of a leak of gas through the diaphragm 36.

In an embodiment, the check valve 312 includes an entry channel 313 of a fixed diameter that is significantly smaller than the diameter of adjacent connecting channels of the entry 67 of the purge line. The entry channel 313 allows the flow of purge gas in the entry direction to be regulated as a function of inlet pressure. Therefore the entry channel 313 allows a proper flow of purge gas in the entry direction without the need of a supplemental regulator for regulating the inlet pressure of the purge gas in the entry 67 of the purge line.

One skilled in the art will understand that other configurations of the sealing assembly 300 than the one described above may be provided for sealing the actuating mechanism 96 of the actuation system 220 and discharge the gas leaked through the diaphragm via the exit of a purge line of the valve. It should be understood that any assembly which results in a sealed separation provided in the valve body to prevent potential leaks from the diaphragm from reaching the actuating mechanism 96 of the actuation system 220 and discharge the gas leaked through the diaphragm via the exit 69 of a purge line of the valve 30 could be used. For example and without being limitative, the sealed closure could be effected using a different combination of diaphragm and/or membrane, or a different configuration of the upper piston.

Figure 15:
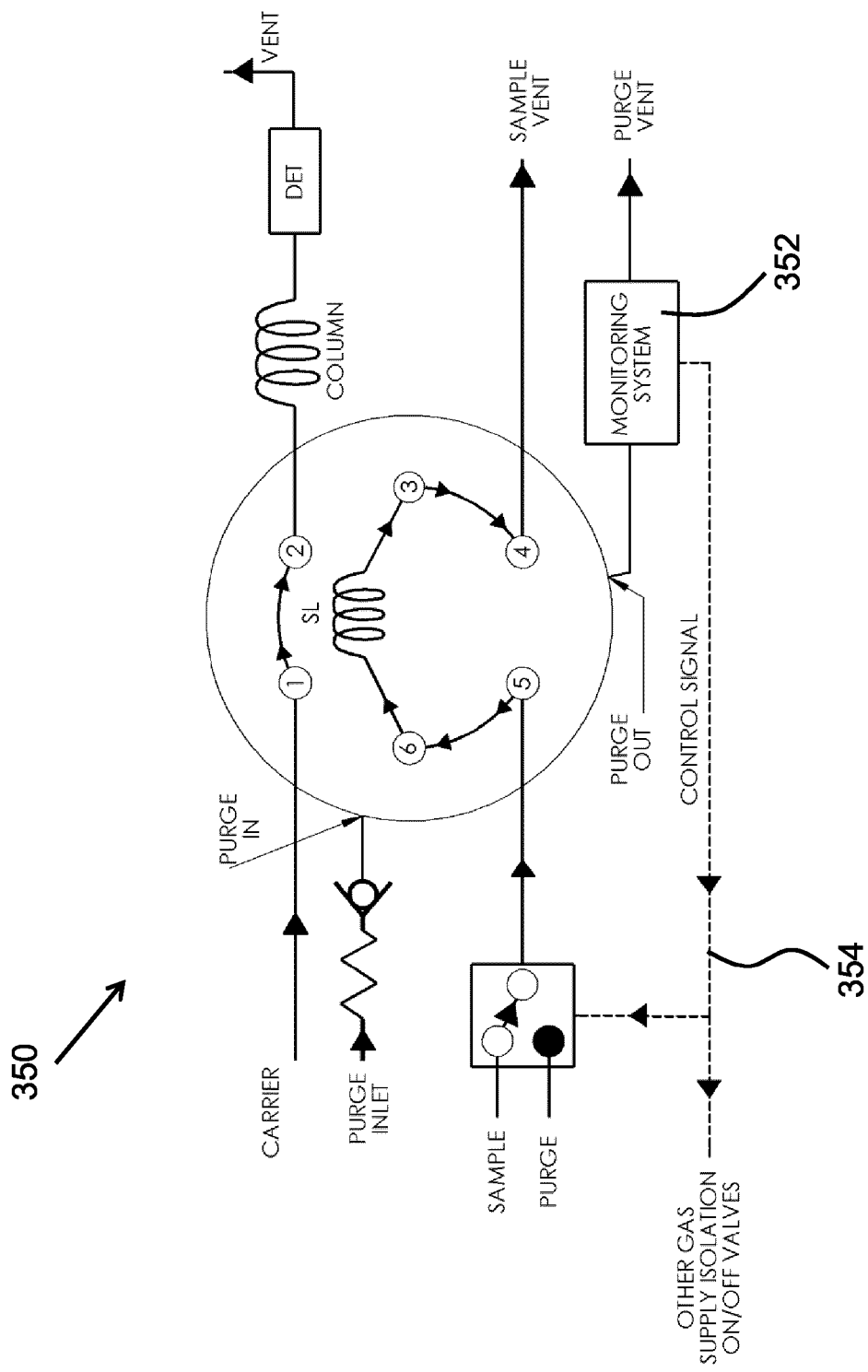
FIG. 15 is a schematic representation of a chromatographic system allowing the detection of a leak of the sample and/or actuation gas through the diaphragm of the valve, according to an embodiment.

In an embodiment, and as can be seen in FIG. 15, a valve with a sealing assembly as described above may be used in a chromatographic system 350 which allows the detection of a leak of the sample and/or actuation gas through the diaphragm and triggering of a leak control procedure. As schematized in FIG. 15, the chromatographic system 350 may be provided with a monitoring system 352 connected to the exit 69 of the purge line and monitoring the pressure and/or purity of the purge gas. In an embodiment, when a variation in the pressure and/or purity of the purge gas is detected by the monitoring system 352 and is such that it is indicative of a leak of the sample and/or actuation gas, the monitoring system 352 generates a control signal 354 that triggers the leak control procedure. For example and without being limitative, in an embodiment, the leak control procedure may initiate the shutting of the gas supply of the valve, the release of an inert gas into the valve, or the like. A signal indicative of a leak, such as, for example, an emergency sound signal, an emergency light or the like, may also be activated to alert an operator of the leak. One skilled in the art will understand that, in alternative embodiments, the leak control procedure may also trigger different or additional operations, for example to indicate that a leak has been detected and/or to minimize the impacts of such a leak.

Locking Mechanism

Figure 4E:
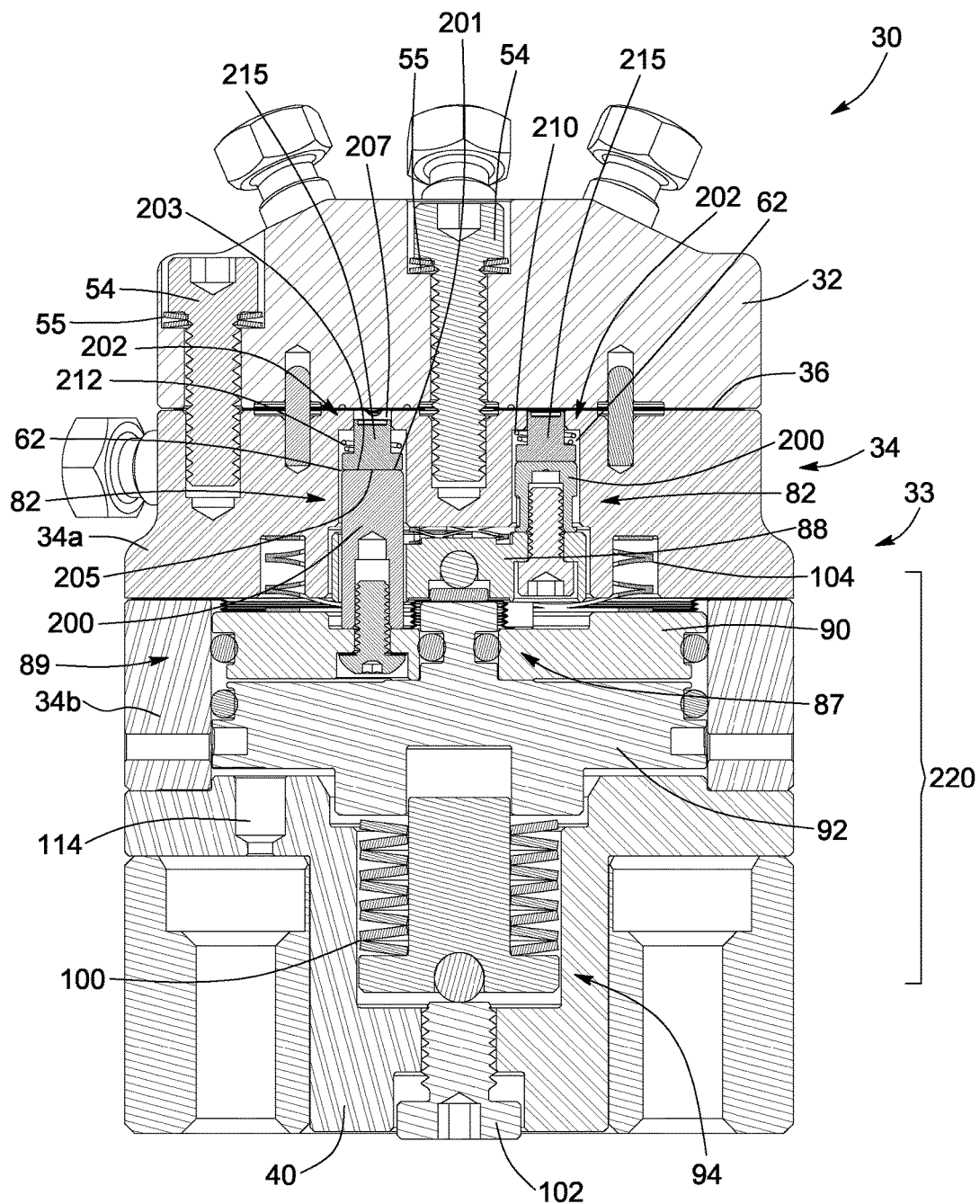
FIG. 4E is also a cross-sectional side view of an embodiment of the diaphragm-sealed valve of FIG. 2 taken along line IV-IV, where the locking pins are removed.

Oftentimes, after diaphragm valves are built and fully tested, they are sealed in plastic packages, packed and stored in inventory before shipping to customers. Depending on various factors such as market demand, inventory management, customer need and the like, valves are likely to stay unused for weeks or months after their manufacture. In addition, in some circumstances a valve owner may temporarily shut down or remove a valve from active use for an undetermined amount of time before putting it in service again. While a valve is idle (as shown in FIG. 4E), its normally closed plungers are in their closed position and therefore apply a constant pressure on the diaphragm. Depending on diaphragm material, this could lead to a permanent deformation of the diaphragm 36, and reduced efficiency of the valve 30. A locking mechanism 119 is therefore advantageous to lock the normally closed base sections 200 of the plungers 82 in their open position (as shown in FIG. 4) when the valve is not in use.

In an embodiment, the locking mechanism 119 advantageously engages the first support structure 87 when the base sections 200 of the normally closed plungers 82 are in an open position, thereby acting against the biasing mechanisms 94 and physically preventing the plungers 82 from reaching a closed position where the top section 202 is pushed against the diaphragm 36. As will be appreciated by one of ordinary skill in the art, the use of such a locking mechanism 119 can advantageously be used to prevent closed plungers 82 from deforming, compressing or otherwise acting upon the diaphragm 36 when the valve 30 is not in use.

It will also be appreciated that such locking mechanism 119 can also advantageously ease replacement of the diaphragm 36 during maintenance and the like. By enabling a user to restrain the normally closed base sections 200 of the plungers within the valve body 33, it can be assured that the plungers do not interfere with the proper positioning of the diaphragm 36.

Different possible embodiments of such a locking mechanism are described in detail in the present Applicant's application PCT/CA2009/001783 which is incorporated herein by reference, and will not, as such, be described further herein.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A valve comprising:
    a valve cap having a plurality of process conduits extending therethrough, each one of the plurality of process conduits ending in a process port at a valve cap interface;
    a valve body defining a valve body interface facing the valve cap interface, the valve body comprising an upper section and a lower section;
    a diaphragm positioned between the valve cap interface and the valve body interface, across the process ports;
    a purge line provided through one of the valve cap and the valve body, the purge line having an entry and an exit;
    a plurality of plungers, each one of the plurality of plungers being positioned in a corresponding plunger passage of a plurality of plunger passages formed in the valve body and being movable between a closed position where the plunger engages the diaphragm, and an open position where the plunger is disengaged from the diaphragm;
    an actuation system for moving each one of the plurality of plungers between the closed position and the open position, the actuation system comprising an upper piston and a lower piston actuated by an actuating mechanism; and
    a sealing assembly located in the valve body, the sealing assembly at least partially extending between the upper section and the lower section of the valve body and being configured and positioned to prevent fluid leaked through the diaphragm from leaking into the actuating mechanism of the actuation system, such that the fluid leaked through the diaphragm is discharged via the exit of the purge line of the valve.

2. The valve of claim 1, wherein the valve further comprises a check valve preventing an upstream flow of fluid leaked through the diaphragm into the entry of the purge line.

3. The valve of claim 1, wherein a circular lip extends from at least one of the valve cap interface and the valve body interface.

4. The valve of claim 1, wherein the sealing assembly comprises a plurality of passage seals, each one of the plurality of passage seals sealing a corresponding one of the plurality of plunger passages.

5. The valve of claim 4, wherein each one of the plurality of passage seals seals the corresponding one of the plurality of plunger passages at an interface between the upper section and the lower section of the valve body.

6. The valve of claim 5, wherein each one of the plurality of plungers comprises a base section and a top section, each one of the passage seals covering the base section of a corresponding one of the plurality of plungers by extending between the base section and the top section of the plunger, in the corresponding plunger passage.

7. The valve of claim 6, wherein the sealing assembly comprises a sealing diaphragm including the plurality of passage seals, the sealing diaphragm being positioned between the upper section and the lower section of the valve body.

8. The valve of claim 7, wherein the sealing diaphragm is a metallic diaphragm.

9. The valve of claim 7, wherein the sealing diaphragm is coated with a protective coating.

10. The valve of claim 6, wherein each one of the plurality of passage seals is configured to expand and retract according to the movement of the base section of the corresponding one of the plurality of plungers.

11. The valve of claim 10, wherein each one of the plurality of passage seals comprises a bellows section.

12. The valve of claim 10, wherein each one of the plurality of passage seals biases the base section of the corresponding one of the plurality of plungers downwards, thereby cooperating with the biasing mechanism to bias the plunger towards an open configuration.

13. The valve of claim 1,
    wherein the sealing assembly comprises:
        a first seal for sealing an interface between the upper piston and the valve body;
        a second seal for sealing an interface between the upper piston and the lower piston; and
        a plurality of third seals for sealing a connection between the upper piston and each one of the plurality of plungers mounted thereto.

14. The valve of claim 13, wherein the first seal is connected at a first end to the upper piston and at a second end to the valve body, the second seal is connected to the upper piston and covers a section of the lower piston extending through the upper piston and each one of the plurality of third seals is located between the upper piston and a head of a mounting structure for mounting one of the plurality of plungers thereto.

15. The valve of claim 13, wherein each one of the first seal, the second seal and the plurality of third seals are metallic seals.

16. The valve of claim 13, wherein at least one of the first seal, the second seal and one of the plurality of third seals is coated with a protective coating.

17. The valve of claim 13, wherein at least one of the first seal and the second seal further comprise a bellows section.

18. A chromatographic system comprising:
    a valve comprising:
        a valve cap having a plurality of process conduits extending therethrough, each one of the plurality of process conduits ending in a process port at a valve cap interface;
        a valve body defining a valve body interface facing the valve cap interface, the valve body comprising an upper section and a lower section;
        a diaphragm positioned between the valve cap interface and the valve body interface, across the process ports;

a purge line provided through one of the valve cap and the valve body, the purge line having an entry and an exit;

a plurality of plungers, each one of the plurality of plungers being positioned in a corresponding plunger passage of a plurality of plunger passages formed in the valve body and being movable between a closed position where the plunger engages the diaphragm, and an open position where the plunger is disengaged from the diaphragm;

an actuation system for moving each one of the plurality of plungers between the closed position and the open position, the actuation system comprising an upper piston and a lower piston actuated by an actuating mechanism; and a sealing assembly located in the valve body, the sealing assembly at least partially extending between the upper section and the lower section of the valve body and being configured and positioned to prevent fluid leaked through the diaphragm from leaking into the actuating mechanism of the actuation system, such that the fluid leaked through the diaphragm is discharged via the exit of the purge line of the valve;

a monitoring system connected to the exit of the purge line of the valve, the monitoring system being configured to monitor a purge gas flowing through the exit of the purge line, detect variations of the purge gas indicative of a fluid leaked through the diaphragm of the valve and trigger a leak control procedure upon detection of the variations of the purge gas indicative of a fluid leaked through the diaphragm of the valve.

19. The chromatographic system of claim 18, wherein the valve further comprises a check valve preventing an upstream flow of fluid leaked through the diaphragm into the entry of the purge line.

20. The chromatographic system of claim 18 or 19, wherein a circular lip extends from at least one of the valve cap interface and the valve body interface.

21. A method of operation of a chromatographic system including a valve such as defined in claim 1, the method comprising the steps of:

monitoring a purge fluid flowing through an exit of a purge line of the valve;

detecting variations of the purge fluid indicative of a fluid leaked through the diaphragm of the valve; and triggering a leak control procedure upon detection of the variations of the purge fluid indicative of a fluid leaked through the diaphragm of the valve.

22. The method of claim 21, wherein the step of monitoring a purge fluid flowing through an exit of a purge line of the valve includes at least one of monitoring a pressure of the purge fluid and monitoring a purity of the purge fluid.

23. The method of claim 21, wherein the step of triggering a leak control procedure upon detection of the variations of the purge fluid indicative of a fluid leaked through the diaphragm of the valve includes at least one of initiating the shutting of a fluid supply of the valve, releasing an inert fluid into the valve and activating a signal indicative of a leak.

* * * * *

UNITED STATES PATENT AND TRADEMARK OFFICE
CERTIFICATE OF CORRECTION

Page 1 of 2

PATENT NO. : 9,632,065 B2
APPLICATION NO. : 14/775195
DATED : April 25, 2017
INVENTOR(S) : Yves Gamache It is certified that error appears in the above-identified patent and that said Letters Patent is hereby corrected as shown below:

On the Title Page

Abstract, Line 13:
"and" should be — an —

In the Specification

Column 2, Line 16:
Delete "phosphine" (2nd occurrence)

Column 2, Line 44:
Delete ","

Column 5, Line 4:
"4D"" should be — 4C" —

Column 5, Line 17:
"C C" should be — C-C —

Column 5, Line 25:
"7C 7C" should be — 7C-7C —

Column 8, Line 42:
"extends" should be — extend —

Column 8, Line 50:
"lip" should be — lips —

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,632,065 B2

Column 11, Line 62:
"transversally" should be — transversely —

Column 15, Line 3:
Delete "that" (2nd occurrence)

Column 16, Line 52:
Delete "that" (2nd occurrence)

In the Claims

Column 21, Claim 18, Line 15:
Delete "and"

Column 21, Claim 18, Line 23:
After "valve;" insert -- and --

Column 22, Claim 20, Line 7:
Delete "or 19"